United States Patent
Burke et al.

(10) Patent No.: US 9,010,522 B2
(45) Date of Patent: Apr. 21, 2015

(54) METHOD AND APPARATUS FOR CONVEYING A CELLULOSIC FEEDSTOCK

(75) Inventors: Murray J. Burke, Oakville (CA);
Sunalie N. Hillier, Georgetown (CA);
Quang A. Nguyen, Chesterfield, MO (US)

(73) Assignee: Abengoa Bioenergy New Technologies, LLC, Chesterfield, MO (US)

( * ) Notice: Subject to any disclaimer, the term of this patent is extended or adjusted under 35 U.S.C. 154(b) by 659 days.

(21) Appl. No.: 12/181,596

(22) Filed: Jul. 29, 2008

(65) Prior Publication Data
US 2010/0028089 A1   Feb. 4, 2010

(30) Foreign Application Priority Data

Jul. 24, 2008 (CA) .................................... 2638160

(51) Int. Cl.
*B65G 47/00* (2006.01)
*B65G 33/18* (2006.01)
*B65G 33/26* (2006.01)

(52) U.S. Cl.
CPC *B65G 33/18* (2013.01); *Y02E 50/16* (2013.01)

(58) Field of Classification Search
CPC .......... B65G 33/18; B01F 7/042; Y02E 50/16
USPC .............. 198/676, 677, 662, 664; 406/53, 55;
366/266, 318, 300, 330.2, 330.1,
366/325.3, 301, 297, 291, 312, 326.1
See application file for complete search history.

(56) References Cited

U.S. PATENT DOCUMENTS

| | | | | |
|---|---|---|---|---|
| 319,299 A | * | 6/1885 | Morgan | 198/665 |
| 459,113 A | * | 9/1891 | Rymal | 416/207 |
| 847,492 A | * | 3/1907 | Morris | 220/23.9 |
| 976,363 A | * | 11/1910 | Hinkhouse | 165/109.1 |
| 1,073,425 A | * | 9/1913 | Lambert | 241/292.1 |

(Continued)

FOREIGN PATENT DOCUMENTS

| | | |
|---|---|---|
| CA | 1070537 | 1/1980 |
| CA | 1096374 B | 2/1981 |

(Continued)

OTHER PUBLICATIONS

International Search Report received on the corresponding international application No. PCT/CA2009/001032, dated Oct. 27, 2009.

(Continued)

*Primary Examiner* — William R Harp
(74) *Attorney, Agent, or Firm* — Armstrong Teasdale LLP

(57) ABSTRACT

An apparatus for conveying a cellulosic feedstock is disclosed. The apparatus comprises an enclosed volume having a lower surface comprising a plurality of longitudinally extending portions. Each longitudinally extending portion has an inner surface that is arcuate in transverse section. A plurality of conveyance members are provided within the enclosed volume. Each conveyance member is associated with one of the inner surfaces and configured to sweep the one of the inner surfaces. Additionally, a method for treating a cellulosic feedstock is disclosed. The method comprises providing a cellulosic feedstock being less than 100% saturated moisture. The cellulosic feedstock is introduced into a longitudinally extending enclosed volume, and conveyed longitudinally through the enclosed volume while being mixed.

26 Claims, 8 Drawing Sheets

(56) References Cited

U.S. PATENT DOCUMENTS

| | | | | |
|---|---|---|---|---|
| 1,106,736 A | * | 8/1914 | Schuler | 198/676 |
| 1,173,825 A | | 2/1916 | McWallen | |
| 1,190,923 A | | 7/1916 | Lindquist | |
| 1,247,153 A | | 11/1917 | Roberts | |
| 1,560,855 A | * | 11/1925 | Queneau | 202/118 |
| 1,767,102 A | * | 6/1930 | Thorne | 366/297 |
| 1,824,221 A | | 9/1931 | Mason | |
| 2,080,327 A | * | 5/1937 | McKinnis | 366/196 |
| 2,086,701 A | | 7/1937 | Dreyfus | |
| 2,263,608 A | | 11/1941 | Brown | |
| 2,333,739 A | | 11/1943 | Puckett | |
| 2,541,058 A | | 2/1951 | Heritage et al. | |
| 2,541,059 A | | 2/1951 | Heritage et al. | |
| 2,541,127 A | | 2/1951 | Van Beckum | |
| 2,570,042 A | | 10/1951 | West | |
| 2,595,827 A | | 5/1952 | Boruff et al. | |
| 2,615,883 A | | 10/1952 | Sweeney et al. | |
| 2,697,703 A | | 12/1954 | Heritage et al. | |
| 2,758,031 A | | 8/1956 | Ozai-Durrani | |
| 2,964,391 A | * | 12/1960 | Benson | 422/134 |
| 3,017,404 A | | 1/1962 | Ball | |
| 3,109,560 A | | 11/1963 | Rosenleaf | |
| 3,199,731 A | | 8/1965 | Brauer et al. | |
| 3,223,697 A | | 12/1965 | Ball et al. | |
| 3,357,437 A | | 12/1967 | Maguire | |
| 3,383,277 A | | 5/1968 | Gordon et al. | |
| 3,407,943 A | | 10/1968 | Douglass, Jr. | |
| 3,572,593 A | | 3/1971 | Guarisco | |
| 3,617,433 A | | 11/1971 | Sutherland | |
| 3,640,509 A | * | 2/1972 | Inamura et al. | 366/300 |
| 3,743,572 A | | 7/1973 | Richter et al. | |
| 3,817,826 A | | 6/1974 | Hoye | |
| 3,828,661 A | * | 8/1974 | Vink | 99/483 |
| 3,964,874 A | * | 6/1976 | Maruko et al. | 422/135 |
| 3,964,880 A | | 6/1976 | Siegrist | |
| 4,023,982 A | | 5/1977 | Knaugh | |
| 4,055,673 A | | 10/1977 | Mueller et al. | |
| 4,062,304 A | * | 12/1977 | Herbold et al. | 110/255 |
| 4,119,025 A | | 10/1978 | Brown | |
| 4,136,207 A | | 1/1979 | Bender | |
| 4,160,695 A | | 7/1979 | Dietrichs et al. | |
| 4,181,796 A | | 1/1980 | Dietrichs et al. | |
| 4,186,658 A | | 2/1980 | Brown | |
| 4,196,827 A | | 4/1980 | Leafdale | |
| 4,200,692 A | | 4/1980 | Puls et al. | |
| 4,211,163 A | | 7/1980 | Brown et al. | |
| 4,237,226 A | | 12/1980 | Grethlein | |
| 4,281,934 A | * | 8/1981 | Krause et al. | 366/30 |
| 4,286,884 A | | 9/1981 | Retrum | |
| 4,296,864 A | | 10/1981 | Misaka et al. | |
| 4,316,748 A | | 2/1982 | Rugg et al. | |
| 4,331,447 A | | 5/1982 | Kamada et al. | |
| 4,341,353 A | | 7/1982 | Hamilton et al. | |
| 4,364,667 A | * | 12/1982 | Reiner | 366/325.3 |
| 4,412,485 A | | 11/1983 | Brown | |
| 4,427,453 A | | 1/1984 | Reitter | |
| 4,432,805 A | | 2/1984 | Nuuttila et al. | |
| 4,436,586 A | | 3/1984 | Elmore | |
| 4,451,567 A | | 5/1984 | Ishibashi et al. | |
| 4,461,648 A | | 7/1984 | Foody | |
| 4,470,851 A | | 9/1984 | Paszner et al. | |
| 4,483,625 A | * | 11/1984 | Fisher | 366/297 |
| 4,511,433 A | | 4/1985 | Tournier et al. | |
| 4,584,057 A | | 4/1986 | Rowe et al. | |
| 4,600,590 A | | 7/1986 | Dale | |
| 4,615,742 A | | 10/1986 | Wright | |
| 4,645,541 A | | 2/1987 | DeLong | |
| 4,667,373 A | | 5/1987 | Roder | |
| 4,670,944 A | | 6/1987 | Thrash | |
| 4,676,363 A | * | 6/1987 | Buchmuller et al. | 198/493 |
| 4,746,404 A | | 5/1988 | Laakso | |
| 4,751,034 A | | 6/1988 | DeLong et al. | |
| 4,752,579 A | | 6/1988 | Arena et al. | |
| 4,764,596 A | | 8/1988 | Lora et al. | |
| 4,775,239 A | * | 10/1988 | Martinek et al. | 366/2 |
| 4,776,703 A | * | 10/1988 | Oda et al. | 366/97 |
| 4,798,651 A | | 1/1989 | Kokta | |
| 4,867,846 A | | 9/1989 | Fleck | |
| 4,869,786 A | | 9/1989 | Hanke | |
| 4,908,098 A | | 3/1990 | Delong et al. | |
| 4,908,099 A | | 3/1990 | DeLong | |
| 4,911,558 A | * | 3/1990 | Teske | 366/300 |
| 4,947,743 A | | 8/1990 | Brown et al. | |
| 4,966,650 A | | 10/1990 | DeLong et al. | |
| 4,997,488 A | | 3/1991 | Gould et al. | |
| 5,012,731 A | | 5/1991 | Maisonneuve | |
| 5,023,097 A | * | 6/1991 | Tyson | 426/271 |
| 5,034,099 A | | 7/1991 | Nilsson | |
| 5,047,332 A | | 9/1991 | Chahal | |
| 5,052,874 A | | 10/1991 | Johanson | |
| 5,100,066 A | | 3/1992 | Frei | |
| 5,114,488 A | | 5/1992 | Huber et al. | |
| 5,122,228 A | | 6/1992 | Bouchette et al. | |
| 5,135,861 A | | 8/1992 | Pavilon | |
| 5,176,295 A | | 1/1993 | Stefanik | |
| 5,181,804 A | | 1/1993 | Wysong et al. | |
| 5,188,298 A | | 2/1993 | Gerber | |
| 5,198,074 A | | 3/1993 | Villavicencio et al. | |
| 5,221,357 A | | 6/1993 | Brink | |
| 5,338,366 A | | 8/1994 | Grace et al. | |
| 5,348,871 A | | 9/1994 | Scott et al. | |
| 5,366,558 A | | 11/1994 | Brink | |
| 5,411,594 A | | 5/1995 | Brelsford | |
| 5,417,492 A | * | 5/1995 | Christian et al. | 366/146 |
| 5,424,417 A | | 6/1995 | Torget et al. | |
| 5,487,989 A | | 1/1996 | Fowler et al. | |
| 5,503,996 A | | 4/1996 | Torget et al. | |
| 5,504,259 A | | 4/1996 | Diebold et al. | |
| 5,536,325 A | | 7/1996 | Brink | |
| 5,571,703 A | | 11/1996 | Chieffalo et al. | |
| 5,597,714 A | | 1/1997 | Farone et al. | |
| 5,611,930 A | | 3/1997 | Nguyen et al. | |
| 5,628,830 A | | 5/1997 | Brink | |
| 5,677,154 A | | 10/1997 | Van Draanen et al. | |
| 5,705,213 A | | 1/1998 | Guillin | |
| 5,705,369 A | | 1/1998 | Torget et al. | |
| 5,730,837 A | | 3/1998 | Black et al. | |
| 5,733,758 A | | 3/1998 | Nguyen | |
| 5,735,916 A | | 4/1998 | Lucas et al. | |
| 5,791,779 A | * | 8/1998 | Smith, Sr. | 366/297 |
| 5,843,760 A | | 12/1998 | Zhang et al. | |
| 5,863,389 A | | 1/1999 | White et al. | |
| 5,916,780 A | | 6/1999 | Foody et al. | |
| 5,932,452 A | | 8/1999 | Mustranta et al. | |
| 6,022,419 A | | 2/2000 | Torget et al. | |
| 6,063,204 A | | 5/2000 | Hester et al. | |
| 6,090,595 A | | 7/2000 | Foody et al. | |
| 6,199,299 B1 | | 3/2001 | Prough et al. | |
| 6,228,177 B1 | | 5/2001 | Torget | |
| 6,330,767 B1 | | 12/2001 | Carr et al. | |
| 6,336,573 B1 | | 1/2002 | Johanson | |
| 6,409,841 B1 | | 6/2002 | Lombard | |
| 6,419,788 B1 | | 7/2002 | Wingerson | |
| 6,423,145 B1 | | 7/2002 | Nguyen et al. | |
| 6,498,029 B2 | | 12/2002 | Keller, Jr. et al. | |
| 6,557,267 B2 | | 5/2003 | Wanger | |
| 6,569,653 B1 | | 5/2003 | Alard et al. | |
| 6,572,734 B2 | | 6/2003 | Baker | |
| 6,620,292 B2 | | 9/2003 | Wingerson | |
| 6,648,251 B1 | | 11/2003 | Chollet | |
| 6,660,506 B2 | | 12/2003 | Nguyen et al. | |
| 6,737,258 B2 | | 5/2004 | Hames et al. | |
| 6,743,928 B1 | | 6/2004 | Zeitsch | |
| 6,846,103 B2 | * | 1/2005 | Okamoto et al. | 366/297 |
| 6,908,995 B2 | | 6/2005 | Blount | |
| 6,927,048 B2 | | 8/2005 | Verser et al. | |
| 7,109,005 B2 | | 9/2006 | Eroma et al. | |
| 7,178,698 B2 | | 2/2007 | Forslund et al. | |
| 7,198,925 B2 | | 4/2007 | Foody | |
| 7,238,242 B2 | | 7/2007 | Pinatti et al. | |
| 7,396,434 B2 | | 7/2008 | Rodriguez Rivera et al. | |
| 7,445,691 B2 | | 11/2008 | Snekkenes et al. | |
| 7,461,591 B2 | | 12/2008 | Babbini | |
| 7,494,675 B2 | | 2/2009 | Abbas et al. | |

(56) References Cited

U.S. PATENT DOCUMENTS

| | | |
|---|---|---|
| 7,503,981 B2 | 3/2009 | Wyman et al. |
| 7,875,444 B2 | 1/2011 | Yang et al. |
| 7,901,511 B2 | 3/2011 | Griffin et al. |
| 7,937,851 B2 | 5/2011 | Rajagopalan et al. |
| 7,993,463 B2 | 8/2011 | Griffin et al. |
| 8,051,986 B2 | 11/2011 | Lees |
| 8,053,566 B2 | 11/2011 | Belanger et al. |
| 8,193,395 B2 | 6/2012 | Fenton et al. |
| 8,449,680 B2 | 5/2013 | Burke et al. |
| 2002/0003032 A1 | 1/2002 | Nay et al. |
| 2002/0164731 A1 | 11/2002 | Eroma et al. |
| 2003/0089465 A1 | 5/2003 | Schaible et al. |
| 2004/0121436 A1 | 6/2004 | Blount |
| 2004/0154760 A1 | 8/2004 | Dean |
| 2004/0171136 A1 | 9/2004 | Holtzapple et al. |
| 2004/0231661 A1 | 11/2004 | Griffin et al. |
| 2004/0231811 A1 | 11/2004 | Engstrand et al. |
| 2005/0269048 A1 | 12/2005 | Rodriguez et al. |
| 2006/0088922 A1 | 4/2006 | Yang et al. |
| 2006/0163118 A1 | 7/2006 | Kelsey et al. |
| 2006/0169430 A1 | 8/2006 | Tarasenko |
| 2006/0188965 A1 | 8/2006 | Wyman et al. |
| 2006/0233864 A1 | 10/2006 | Power |
| 2006/0272518 A1 | 12/2006 | Babbini |
| 2006/0275895 A1 | 12/2006 | Jensen et al. |
| 2007/0037267 A1 | 2/2007 | Lewis et al. |
| 2007/0148751 A1 | 6/2007 | Griffin et al. |
| 2007/0209974 A1 | 9/2007 | Lees |
| 2007/0215300 A1 | 9/2007 | Upfal et al. |
| 2007/0218530 A1 | 9/2007 | Duck et al. |
| 2007/0227063 A1 | 10/2007 | Dale et al. |
| 2008/0026431 A1 | 1/2008 | Saito et al. |
| 2008/0038784 A1 | 2/2008 | D'Arnaud-Taylor |
| 2008/0227161 A1 | 9/2008 | Levie et al. |
| 2009/0029432 A1 | 1/2009 | Abbas et al. |
| 2009/0062516 A1 | 3/2009 | Belanger et al. |
| 2009/0069550 A1 | 3/2009 | Belanger et al. |
| 2009/0098616 A1 | 4/2009 | Burke et al. |
| 2009/0098617 A1 | 4/2009 | Burke et al. |
| 2009/0240088 A1 | 9/2009 | Fenton et al. |
| 2009/0246848 A1 | 10/2009 | Noel |
| 2010/0024806 A1 | 2/2010 | Burke et al. |
| 2010/0024807 A1 | 2/2010 | Burke et al. |
| 2010/0024808 A1 | 2/2010 | Burke et al. |
| 2010/0024809 A1 | 2/2010 | Burke et al. |
| 2010/0124583 A1 | 5/2010 | Medoff |
| 2010/0186735 A1 | 7/2010 | Burke et al. |
| 2010/0186736 A1 | 7/2010 | Burke et al. |
| 2011/0011391 A1 | 1/2011 | Burke |
| 2012/0111321 A1 | 5/2012 | Nguyen et al. |

FOREIGN PATENT DOCUMENTS

| | | |
|---|---|---|
| CA | 1147105 A | 5/1983 |
| CA | 1173825 | 9/1984 |
| CA | 1190923 | 7/1985 |
| CA | 1267407 | 3/1990 |
| CA | 1287705 | 8/1991 |
| CA | 2037275 A1 | 8/1992 |
| CA | 1322366 C | 9/1993 |
| CA | 2063547 A1 | 9/1993 |
| CA | 2065939 A1 | 10/1993 |
| CA | 2339002 A1 | 7/1999 |
| CA | 2638150 A1 | 1/2010 |
| CA | 2638159 A1 | 1/2010 |
| CN | 200981760 | 11/2007 |
| EP | 0487793 A1 | 6/1992 |
| EP | 0884391 B1 | 1/2002 |
| EP | 1316620 A2 | 6/2003 |
| EP | 1036236 B1 | 7/2003 |
| FR | 777824 | 3/1935 |
| GB | 892506 | 3/1962 |
| GB | 1043460 A | 9/1966 |
| WO | 9213849 A1 | 8/1992 |
| WO | 9640970 A1 | 12/1996 |
| WO | 9732073 A1 | 9/1997 |
| WO | 0238787 A2 | 5/2002 |
| WO | 2004018645 A2 | 3/2004 |
| WO | 2004081193 A2 | 9/2004 |
| WO | 2004106624 A1 | 12/2004 |
| WO | 2005079190 A2 | 9/2005 |
| WO | 2005118165 A1 | 12/2005 |
| WO | 2006017655 A3 | 2/2006 |
| WO | 2006034591 A1 | 4/2006 |
| WO | 2006055362 A1 | 5/2006 |
| WO | 2006063467 A1 | 6/2006 |
| WO | 2007009463 A2 | 1/2007 |
| WO | 2007064296 A1 | 6/2007 |
| WO | 2007065241 A1 | 6/2007 |
| WO | 2007111605 A1 | 10/2007 |
| WO | 2008086115 A2 | 7/2008 |
| WO | 2008144903 A1 | 12/2008 |
| WO | 2009012779 A2 | 1/2009 |
| WO | 2009018469 A1 | 2/2009 |
| WO | 2009089439 A1 | 7/2009 |
| WO | 2010006840 A2 | 1/2010 |
| WO | 2010009547 A1 | 1/2010 |
| WO | 2010009548 A1 | 1/2010 |
| WO | 2010009549 A1 | 1/2010 |
| WO | 2010009550 A1 | 1/2010 |
| WO | 2010009551 A1 | 1/2010 |
| WO | 2010083600 A1 | 7/2010 |
| WO | 2010083601 A1 | 7/2010 |
| WO | 2011028554 A1 | 3/2011 |

OTHER PUBLICATIONS

Q.A. Nguyen et al., "NREL/DOE Ethanol Pilot-Plant: Current Status and Capabilities" (1996) 58 Bioresource Technology 189.

R.P. Overend & E. Chornet, "Fractionation of lignocellulosics by steam-aqueous pretreatments" (1987) 321 Phil. Trans. R. Soc. Lond. A. 523.

D. Ballerini et al., "Ethanol Production from Lignocellulosics: Large Scale Experimentation and Economics" (1994) 50 Biousource Technology 17.

K.M.F. Kazi, P. Jollez, & E. Chornet, "Preimpregnation: An Important Step for Biomass Refining Processes" (1998) 15:2 Biomass and Bioenergy 125.

M.P. Tucker et al., "Comparison of Yellow Poplar Pretreatment Between NREL Digester and Sunds Hydrolyzer" (1998) 70-72 Applied Biochemistry and Biotechnology 25.

Charles E. Wyman et al., "Comparative Sugar Recovery Data from Laboratory Scale Application of Leading Pretreatment Technologies to Corn Stover" (2005) 96 Bioresource Technology 2026.

Charles E. Wyman et al., "Coordinated Development of Leading Biomass Pretreatment Technologies" (2005) 96 Bioresource Technology 1959.

Nathan Mosier et al., "Features of Promising Technologies for Pretreatment of Lignocellulosic Biomass" (2005) 96 Biosource Technology 673.

Tim Eggeman & Richard T. Elander, "Process and Economics Analysis of Pretreatment Technologies" (2005) 96 Bioresource Technology 2019.

Abengoa Bioenergy, Press Release, "Abengoa Bionergy Awarded DOE Financial Assistance Agreement" (Feb. 28, 2007), online: Abongoa Bioenergy <http://www.abengoabioenergy.es/corp/web/en/acerca_de/sala_de_prensa/historico/2007/20070228_noticias.html#>.

Outputs from the EPOBIO Workshop, Greece, "Products from Plants—From Crops and Forests to Zero Waste Biorefineries" (May 15-17, 2007).

Abengoa Bioenergy, Press Release, "Abengoa Bionergy Opens Pilot Plant for the Energy of the Future" (Oct. 15, 2007), online: Abengoa Bioenergy <http://www.abengoabioenergy.es/corp/web/en/acerca_de/sala_de_prensa/historico/2007/20071015_noticias.html#>.

Merrick & Company, Final Report of Jun. 14, 1999, "Softwood Biomass to Ethanol Feasibility Study" (Aug. 2004) Subcontractor Report published by National Renewable Energy Laboratory.

(56) References Cited

OTHER PUBLICATIONS

Merrick & Company, Final Report of Jan. 2000, "Building a Bridge to the Corn Ethanol Industry. Corn Stover to Ethanol at High Plains Corporation's York, Nebraska Co-Located Plant site".

Melvin P. Tucker et al., "Conversion of Distiller's Grain into Fuel Alcohol and a Higher-Value Animal Feed by Dilute-Acid Pretreament" (2004) 113-116 Applied Biochemistry and Biotechnology 1139.

Melvin P. Tucker et al., "Effects of Temperature and Moisture on Dilute-Acid Steam Explosion Pretreatment of Corn Stover and Cellulase Enzyme Digestibility" (2003) 105-108 Applied Biochemistry and Biotechnology 165.

Kyoung Heon Kim et al., "Continuous Countercurrent Extraction of Hemicellulose from Pretreated Wood Residues" (2001) 91-93 Applied Biochemistry and Biotechnology 253.

Quang A. Nguyen et al., "Two-Stage Diute-Acid Pretreatment of Softwoods" (2000) 84-86 Applied Biochemistry and Biotechnology 561.

Daniel J. Schell et al., "Dilute-Sulfuric Acid Pretreatment of Corn Stover in Pilot-Scale Reactor" (2003) 105-108 Applied Biochemistry and Biotechnology 69.

Q.A. Nguyen & J.N. Saddler, "An Integrated Model for the Technical and Economic Evaluation of an Enzymatic Biomass Conversion Process" (1991) 35 Bioresource and Technology 275.

Q.A. Nguyen et al., "Dilute Acid Pretreatment of Softwoods", Scientific Note, (1998) 70-72 Applied Biochemistry and Biotechnology 77.

Q.A. Nguyen et al., "Dilute Acid Hydrolysis of Softwoods", Scientific Note, (1999) 77-79 Applied Biochemistry and Biotechnology 133.

Raphael Katzen & Donald F. Othmer, "Wood Hydrolysis. A Continuous Process" (1942) 34 Industrial and Engineering Chemistry 314.

"Transactions of the Institution of Chemical Engineers" (1993) 11 Institution of Chemical Engineers, London, the United Kingdom.

Diane Knappert, Hans Grethlein & Alvin Converse, "Partial Acid Hydrolysis of Cellulosic Materials as a Pretreatment for Enzymatic Hydrolysis" (1980) 22 Biotechnology and Bioengineering 1449.

Sung Bae Kim & Y.Y. Lee, "Diffusion of Sulfuric Acid within Lignocellulosic Biomass Particles and its Impact on Dilute-Acid Pretreatment" (2002) 83 Bioresource Technology 165.

Alan W. Roberts, "Design Considerations and Performance Evaluation of Screw Conveyors", online: The South African Institute of Materials Handling <http://www.saimh.co.za/beltcon/beltcon11/beltcon1114.htm>.

National Renewable Energy Laboratory, "Process Design and Cost Estimate of Critical Equipment in the Biomass to Ethanol Process. Acid Hydrolysis Reactors Batch Systems", Report (Seattle, Washington: Harris Group Inc., 2001).

Osamu Kitani & Carl W.. Hall, eds., "Biomass Handbook" 470-474 (Gordon and Breach Science Publishers: New York).

Buell Classifier Fisher-Klosterman, Leaflet, "Operation Principles and Efficiency".

Process Sensors Corporation, "On-Line Moisture Measurement and Control Manufacturing Industries Worldwide", Product Information, online: Process Sensors Corporation <http://processsensors.com/index.html?gclid=CKT27fXvJ0CFREWagodclkUcw>.

Roger M. Rowell, Raymond A. Young, & Judith K. Rowell, eds., Paper and Composites from Agro-Based Resources (Lewis Publishers).

G.H.Emert et al., "Gasohol/Biomass Developments: Economic Update of the Gulf Cellulose Alcohol Process" (Sep. 1980) Chemical Engineering Progress 47.

Ron Kotrba, "The Project of a Lifetime" (Feb. 2006), Ethanol Producer Magazine.

National Renewable Energy Laboratory, "Research Advances: NREL Leads the Way. Cellulosic Ethanol", Brochure, (Mar. 2007), online: National Renewable Energy Laboratory <http://www.nrel.gov/biomass/pdfs/40742.pdf>.

National Renewable Energy Laboratory, Fact Sheet, "Clean Cities: Ethanol Basics" (Oct. 2008), online: U.S. Department of Energy <www.afdc.energy.gov/afdc/pdfs/43835.pdf>.

Brent D. Yacobucci, "Fuel Ethanol: Background and Public Policy Issues", (Mar. 3, 2006), CRS Report for Congress, online: U.S. Department of State, Foreign Press Centre <fpc.state.gov/documents/organization/62837.pdf>.

U.S. Department of Energy, Energy Efficiency & Renewable Energy, Alternative Fuels & Advanced Vehicles Data Center, Article, "Ethanol Market Penetration", online: U.S Department of Energy <http://www.afdc.energy.gov/afdc/ethanol/market.html>.

Kenneth W.Britt, ed., "Handbook of Pulp and Paper Technology", 2nd. ed. (New York: Van Nostrand Reinhold Company).

A. Aden et al., "Lignocellulosic Biomass to Ethanol Process Design and Economics Utilizing Co-Current Dilute Acid Prehydrolysis and Enzymatic Hydrolysis for Corn Stover", (Jun. 2002), Technical Report published by National Renewable Energy Laboratory.

U.S. Department of Energy Office of Science, Genomics Science Program, "Fuel Ethanol Production", online: U.S. Department of Energy Office of Science <http://genomicscience.energy.gov/biofuels/ethanolproduction.shtml>.

Metso Automation, Metso Automation's Newsletter for Neles and Jamesbury products, "Biofuels—a growth market for Metso", (Summer 2008), online: Metso <http://valveproducts.metso.com/metsoautomation/DocDB/catalogs/catalog.taf?pg_parent=397>.

SunOpta Inc., News Release, "SunOpta Announces Sale of Cellulosic Ethanol Facility to China Resources Alcohol Corporation", (Jun. 23, 2006), online: SunOpta Inc. <http://investor.sunopta.com/releasedetail.cfm?ReleaseID=287111>.

Ralph P. Overend, Slideshow, "The Lignocellulosic bottleneck: material properties, architecture and pretreatment".

Robert Wooley et al., "Lignocellulosic Biomass to Ethanol Process Design and Economics Utilizing Co-Current Dilute Acid Prehydrolysis and Enzymatic Hydrolysis Current and Futuristic Scenarios", (Jul. 1999), National Renewable Energy Laborator. Technical Report.

Nathan S. Masier, "Cellulosic Ethanol—Biofuel Beyond Corn" Bio Energy, Purdue University.

U.S Securities and Exchange Commission, "Annual Report Under Section 13 or 15(d) of the Securities Exchange Act of 1934", for Bluefire Ethanol Fuels, Inc. Signed on Feb. 28, 2008.

U.S Securities and Exchange Commission, "Annual Report Under Section 1 or (15)d of the Securities Exchange Act of 1934", for CleanTech Biofuels, Inc. Signed on Mar. 28, 2008.

Schell et al., Dilute-sulfuric acid pretreatment of corn stover in pilot-scale reactor, 2003, Humana Press Inc., vol. 105, No. 1-3, pp. 69-85.

International Search Report received on the corresponding international application No. PCT/CA2009/001035, dated Nov. 5, 2009.

Brownell et al., "Steam-Explosion Pretreatment of Wood: Effect of Chip Size, Acid, Moisture Content and Pressure Drop", Biotechnology and Bioengineering, vol. 28 pp. 792-801 (1986).

Cullis et al. Effect of Initial Moisture Content and Chip Size on the Bioconversion Efficiency of Softwood Lignocellulosics; Biotechnology and Bioengineering, vol. 85, No. 4, pp. 413-421, (2004).

Duff et al., "Bioconversion of forest products industry waste cellulosics to fuel ethanol: A review", Bioresource Technology, vol. 5 pp. 1-33 (1996).

PCT International Search Report, dated Oct. 8, 2012, corresponding to International application No. PCT/CA2010/001091.

Written Opinion of the International Searching Authority, dated Oct. 8, 2010, corresponding to International application No. PCT/CA2010/001091.

Office Action on co-pending Canadian Application 2,638,152 dated Feb. 8, 2011.

International Search Report and Written Opinion received on the corresponding international application No. PCT/CA2009/001033, mailed on Oct. 30, 2009.

"Biofuels Pilot Plant Under Way," Newsbriefs, Chemical Week, Oct. 13-20, 2008, p. 4.

"Easy Steps for Optimal Yeast Rehydration," Laboratory Protocol, Scott Laboratories, Petaluma CA, 1 page.

"Enzyme Sugar-Ethanol Platform Project," NREL, U.S. Dept. of Energy by Midwest Research Institute, Battelle, Bechtel, 47 pages.

(56) References Cited

OTHER PUBLICATIONS

"Ethanol Annual Report FY 1990", SERI, TP-231/3996, Prepared for the U.S. DOE, Jan. 1991, Contract No. DE-AC02-83CH10093, Texeira, R.H. and Goodman, B.J., editors, 344 pages.
"Lessons Learned from Existing Biomass Power Plants," Feb. 2000, NREL/SR-570-26946, G. Wiltsee, Appel Consultants, Inc, Valencia, CA, 149 pages.
"Process Design and Cost Estimate of Critical Equipment in the Biomass to Ethanol Process," Subcontract ACO-9-29067-01, Acid Hydrolysis Reactors Batch System, Report 99-10600/18, NREL, (Prepared by Harris Group Inc., Seattle, Washington, 2001), 36 pages.
"Types of Lignin and Their Properties," 2001, Information Service from the Lignin Institute, 9/1:4 pages, www.lignin.org/01augdialogue.html.
Abstract of Chinese Patent Application CN 101310879 A, 2008, Institute of Process Engineering, Chinese Academy of Sciences.
Activator 90, Product Brochure, 2009, Loveland Products Inc., No. 6566_05/09, 1 page.
Al-Halaly, A.S.M., "A Study of Some Anatomical Chemical Properties and Specific Gravity of *Casuarina equisetifolia* Forst. Wood Grown in Iraq," 1985, AGRIS Record No. IQ8500239, Abstract, 1 page.
Amistco Tower Trays, Product Brochure, Amistco Separation Products, Inc., 8 pages.
Antongiovanni, M., et al., "Variability in Chemical Composition of Straws," 1991, CIHEAM—Options Mediterraneennes, Serie Seminaires, 16:49-53.
Awafo, V.A., et al., "Evaluation of Combination Treatments of Sodium Hydroxide and Steam Explosion for the Production of Cellulase-Systems by Two *T. reesei* Mutants Under Solid-State Fermentation Conditions," 2000, Bioresource Tech, 73:235-245.
Azadbakht, M., et al., "Preparation of Lignin From Wood Dust as Vanillin Source and Comparison of Different Extraction Methods," Oct. 2004, Int J of Biol and Biotech, 1/4:535-537, Abstract Only, 1 page.
Bakker, R. R., et al., "Biofuel Production from Acid-Impregnated Willow and Switchgrass," 2nd World Conference on Biomass for Energy, Industry and Climate Protection, May 10-14, 2004, Rome, Italy, pp. 1467-1470.
Bigelow, M., et al., "Cellulase Production on Bagasse Pretreated with Hot Water," 2002, App Biochem and Biotech, 98-100:921-934.
Coons, R., "DSM Launches Cellulosic Biofuel Project," Oct. 27, 2008, Chemical Week, 170/33:9.
Coons, R., "Novozymes Ramps Up Focus on Second-Generation Biofuels," Oct. 27, 2008, Chemical Week, 170/33:30.
Cunningham, R.L., et al., "Improved Hemicellulose Recovery From Wheat Straw," 1985, Biotech and Bioeng Symp No. 15, Seventh Symposium on Biotechnology for Fuels and Chemicals, pp. 17-26.
Dasari, R.K., et al., "The Effect of Particle Size on Hydrolysis Reaction Rates and Rheological Properties in Cellulosic Slurries," 2007, Appl Biochem and Biotech, Session 2, 137-140/1-2, 289-299, Abstract Only.
De Castro, F.B., "The Use of Steam Treatment to Upgrade Lignocellulosic Materials for Animal Feed," 1994, Thesis, University of Aberdeen, 214 pages.
Dowe, N., et al., "SSF Experimental Protocols-Lignocellulosic Biomass Hydrolysis and Fermentation, Laboratory Analytical Procedure (LAP)," Jan. 2008, NREL Technical Report, NREL/TP-510-42630, 19 pages.
Esteghlalian, A., et al., "Modeling and Optimization of the Dilute-Sulfuric-Acid Pretreatment of Corn Stover, Poplar and Switchgrass," 1997, Bioresource Technology, 59:129-136.
Fan, L.T., et al., "Evaluation of Pretreatments for Enzymatic Conversion of Agricultural Residues," 1981, Biotechnology & Bioengineering Symposium, 11:29-45 (Proceedings of the Third Symposium on Biotechnology in Energy Production and Conservation, Gatlinburg, TN, May 12-15, 1981).
Flexitray Valve Trays, Product Brochure, Koch-Glitsch, Bulletin FTCVT-01, Revised Mar. 2010, 12 pages.
Flint, S.I., et al., "Recovery of Lignin During Nonstarch Polysaccharide Analysis," 1992, Cereal Chem, 69/4:444-447.
Foody, P., "Optimization of Steam Explosion Pretreatment," 1980, Final Report to DOE, Report No. DOE/ET23050-1, Contract No. AC02-79ET23050, Bibliographic Citation, 1 page.
Fuel Ethanol Application Sheet, "CELLIC Ctec and Htec2—Enzymes for Hydrolysis of Lignocellulosic Materials," Novozymes A/S, Luna No. 2010-01668-01, 9 pages.
Gea Wiegand, GmbH, Process Engineering Division, "Bioethanol Technology", Ettlingen, Germany, Company Brochure, 16 pages.
Gea Wiegand, GmbH, Process Engineering Division, "Distillation Technology", Ettlingen, Germany, Company Brochure, 16 pages.
Ghose, T.K., "Measurement of Cellulase Activities," 1987, Pure and Appl. Chem., 59/2:257-268.
Grethlein, H.E., "Chemical Breakdown of Cellulosic Materials," 1978, J. Appl. Chem. Biotechnol. 28:296-308.
Grethlein, H.E., et al., "Common Aspects of Acid Prehydrolysis and Steam Explosion for Pretreating Wood," 1991, Bioresource Technology, 36:77-82.
Grohmann, K., et al., "Optimization of Dilute Acid Pretreatment of Biomass," Proceedings of the Seventh Symposium on Biotechnology for Fuels and Chemicals, May 14-17, 1986, 24 pages.
Hames, B., et al., "Determination of Protein Content in Biomass, Laboratory Analytical Procedure (LAP)," May 2008, NREL Technical Report, NREL/TP-510-42625, 8 pages.
Hames, B., et al., "Preparation of Samples for Compositional Analysis, Laboratory Analytical Procedure (LAP)," Aug. 2008, NREL Technical Report, NREL/TP-510-42620, 12 pages.
International Search Report and the Written Opinion issued in connection with PCT Application No. PCT/CA2009/001032, mailed on Oct. 27, 2009, 11 pages.
International Search Report and the Written Opinion issued in connection with PCT Application No. PCT/CA2009/001036, dated Nov. 13, 2009, 6 pages.
International Search Report and the Written Opinion issued in connection with PCT Application No. PCT/CA2010/000087, mailed on May 4, 2010, 10 pages.
International Search Report and the Written Opinion issued in connection with PCT Application No. PCT/CA2010/000088, mailed on May 14, 2010, 15 pages.
International Search Report issued in connection with PCT Application No. PCT/CA2010/000088, mailed as a corrected version on Jun. 17, 2010.
International Search Report and the Written Opinion issued in connection with PCT Application No. PCT/US2010/46561, dated Dec. 20, 2010, 16 pages.
International Search Report and the Written Opinion issued in PCT Application No. PCT/CA2009/001034, dated Oct. 20, 2009, 9 pages.
International Preliminary Report of Patentability issued in connection with International Application No. PCT/CA2009/001034, issued on Jan. 25, 2011.
International Search Report and the Written Opinion issued in PCT Application No. PCT/US2012/022552, dated May 15, 2012, 18 pages.
Juhasz, T., et al., "Characterization of Cellulases and Hemicellulases Produced by *Trichoderma reesei* on Various Carbon Sources," 2005, Process Biochem, 40:3519-3525.
Keller, F.A., et al., "Yeast Adaptation on Softwood Prehydrolysate," 1998, Appl Biochem and Biotech, 70-72:137-148.
Kolar, L, et al., "Agrochemical Value of Organic Matter of Fermenter Wastes in Biogas Production," 2008, Plant Soil Environ, 54/8:321-328.
Kumar, R., et al., "The Impact of Dilute Sulfuric Acid on the Selectivity of Xylooligomer Depolymerization to Monomers," 2008, Carbohydrate Res, 343:290-300.
Linde, M., et al., "Steam Pretreatment of Acid-Sprayed and Acid-Soaked Barley Straw for Production of Ethanol," 2006, Appl Biochem and Biotech, 129-132:546-562.
Liu, H., et al., "Lignin-Metal Complexation to Eliminate Nonproductive Enzyme Adsorption by Lignin in Unwashed Lignocellulosic Substrates," 2010, 32nd Symposium on Biotechnology for Fuels and Chemicals, 28 pages.

(56) References Cited

OTHER PUBLICATIONS

Ohgren, K., et al., "High Temperature Enzymatic Prehydrolysis Prior to Simultaneous Saccharification and Fermentation of Steam Pretreated Corn Stover for Ethanol Production," 2007, Enzyme Microb Technol, 40/4:607-613.
Pan, X., et al., "Bioconversion of Hybrid Poplar to Ethanol and Co-Products Using an Organosolv Fractionation Process: Optimization of Process Yields," 2006, Biotech and Bioeng, 94/5:851-861.
Propax Yeast Propagation Technology, Product Brochure, Meura S.A., Edited 2009, 2 pages.
Ramsay, J.A., et al., "Biological Conversion of Hemicellulose to Propionic Acid," 1998, Enzyme Microb Technol, 22:292-295.
Schell, D.J., et al., "A Bioethanol Process Development Unit: Initial Operating Experiences and Results with a Corn Fiber Feedstock," 2004, Bioresource Technology, 91:179-188.
Sharma-Shivappa, R.R., et al, "Conversion of Cotton Wastes to Bioenergy and Value-Added Products," 2008, Transactions of the ASABE, 51/6:2239-2246.
Silwet L-77 Surfactant, Specimen Label, Helena Chemical Company, Copyright 2006, 2 pages.
Sluiter, A., et al., "Determination of Ash in Biomass, Laboratory Analytical Procedure (LAP)," NREL Technical Report, NREL/TP-510-42622, Jan. 2008, 8 pages.
Sluiter, A., et al., "Determination of Extractives in Biomass, Laboratory Analytical Procedure (LAP)," NREL Technical Report, NREL/TP-510-42619, Jan. 2008, 12 pages.
Sluiter, A., et al., "Determination of Structural Carbohydrates and Lignin in Biomass, Laboratory Analytical Procedure (LAP)," NREL Technical Report, NREL/TP-510-42618, Apr. 2008, 16 pages.
Sluiter, A., et al., "Determination of Sugars, Byproducts, and Degradation Products in Liquid Fraction Process Samples, Laboratory Analytical Procedure (LAP)," NREL Technical Report, NREL/TP-510-42623, Jan. 2008, 14 pages.
Sluiter, A., et al., "Determination of Total Solids in Biomass and Total Dissolved Solids in Liquid Process Samples, Laboratory Analytical Procedure (LAP)," NREL Technical Report, NREL/TP-510-42621, Mar. 2008, 9 pages.
Sun, L., "Silicon-Based Materials from Rice Husks and Their Applications," 2001, Ind Eng Chem Res, 40/25:5861-5877, Abstract Only, 1 page.
Superfrac High Performance Trays, Product Brochure, Koch-Glitsch, Bulletin KGSF-1, Revised Mar. 2010, 16 pages.
Taherzadeh, M. J. et al., "Pretreatment of Lignocellulosic Wastes to Improve Ethanol and Biogas Production: A Review," 2008, Int. J. Mol. Sci., (9) 1621-1651.
Teleman, et al., "Progress-Curve Analysis Shows that Glucose Inhibits the Cellotriose Hydrosysis Catalysed by Cellobiohydrolase II from *Trichoderma reesi*," 1995, European J Biochem, 231:250-258.
The Artisan Dualflo Tray, Product Brochure, Artisan Industries, Inc., Bulletin 9801, Edit Date Apr. 17, 2003, 2 pages.
Thomas, S., et al., "Biofuels Program C-Milestone Completion Report," FY02, DOE Biofuels Program, Report #373, 2002, 51 pages.
Thomas, S.R., "Corn Stover Feedstock Variability," 2005, Feedstock Area Stage Gate Review Meeting, 34 pages.
Thompson, D.N., et al., "Post-Harvest Processing Methods for Reduction of Silica and Alkali Metals in Wheat Straw," 2002, 24th Symposium on Biotechnology for Fuels and Chemicals, Poster #1-30, 21 pages.
Viamajala, S., et al., "Catalyst Transport in Corn Stover Internodes," 2005, Appl Biochem and Biotech, 129-132:509-527.
Weiss, N.D., et al., "Catalyst Impregnation for High Solids Biomass Pretreatment," 2008, AIChE Annual Meeting, 24 pages.
Yang, B., et al., "Chapter 6. Unconventional Relationships for Hemicellulose Hydrolysis and Subsequent Cellulose Digestion," 2004, Lignocellulose Biodegradation, ACS Symposium Series 889, American Chemical Society, pp. 100-125.
Zimbardi, F., et al., "Acid Impregnation and Steam Explosion of Corn Stover in Batch Processes," 2007, Ind Crops and Products, 26:195-206.

* cited by examiner

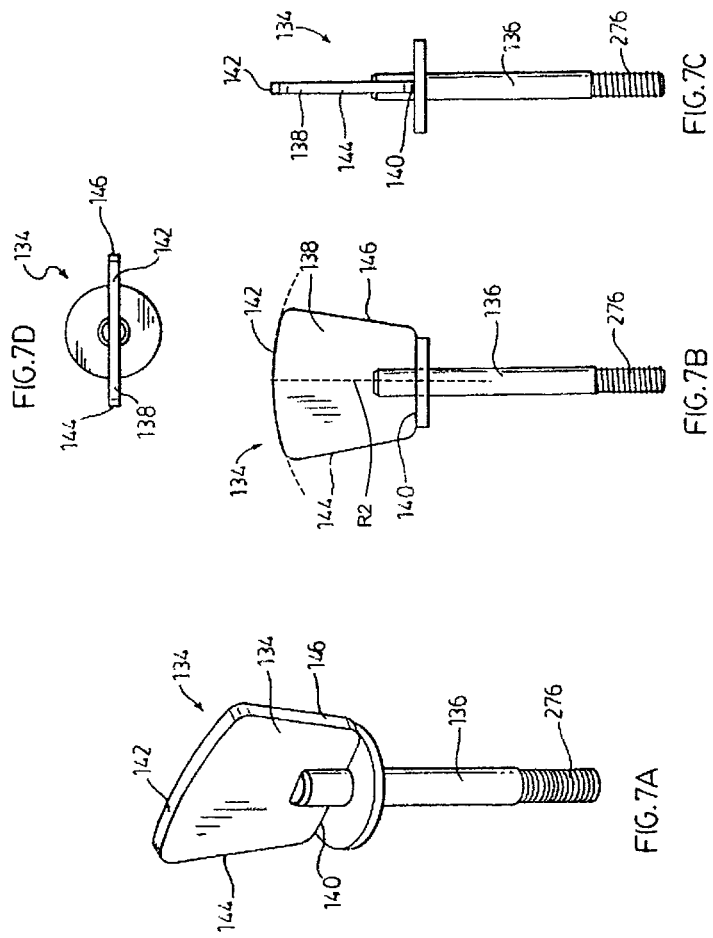

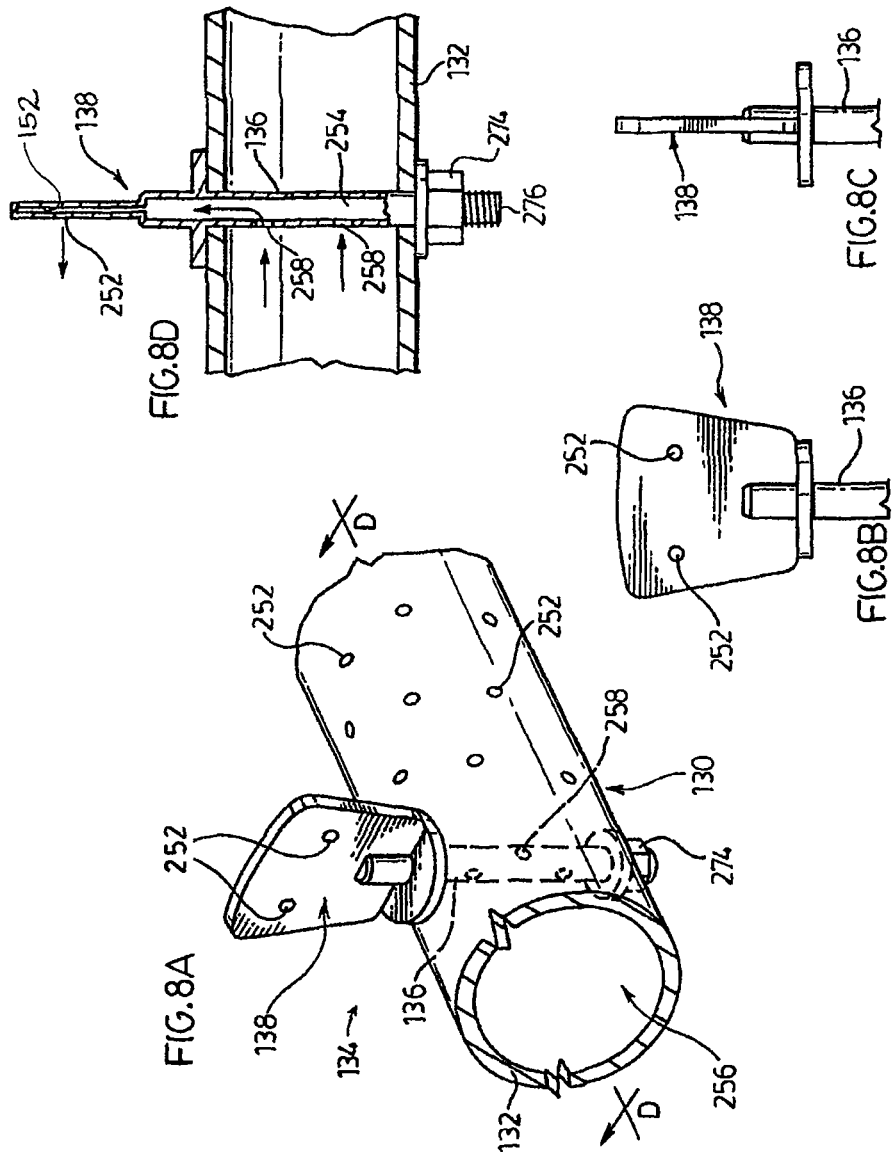

METHOD AND APPARATUS FOR CONVEYING A CELLULOSIC FEEDSTOCK

FIELD

The invention relates to a method and apparatus for preparing a cellulosic feedstock for the subsequent production of a fermentable sugar stream from the cellulose and hemicellulose in the cellulosic feedstock wherein the fermentable sugar stream may be used for subsequent ethanol production. More specifically, the invention relates to a method and apparatus for treating a cellulosic feedstock by mixing and heating the cellulosic feedstock.

BACKGROUND

Several processes for the production of ethanol are known. Generally, the production of fuel ethanol involves the fermentation of sugars with yeast. Typically, the sugars are derived from grains, such as corn and wheat. The starches in the grains are subjected to enzymatic hydrolysis in order to produce the sugars, which are then subjected to fermentation to produce ethanol.

Plant materials are a significant source of fermentable sugars, such as glucose that can be transformed into biofuels. However, the sugars in plant materials are contained in long polymeric chains of cellulose and hemicellulose. Utilizing current fermentation processes, it is necessary to break down these polymeric chains into monomeric sugars, prior to the fermenting step.

Recently, processes have been developed for utilizing plant materials, such as corncobs, straw, and sawdust, to produce sugars for ethanol fermentation. Such processes typically comprise pre-treating the feedstock to increase the accessibility of the cellulose to hydrolysis enzymes, and subjecting the cellulose to cellulase enzyme systems to convert the cellulose into glucose.

Methods of converting plant biomass into fermentable sugars are known in the art and in general comprise two main steps: a pre-treatment step to activate the plant structure, and an enzymatic or chemical hydrolysis step to convert the polymeric chains of cellulose and hemicellulose into monomeric sugars. Several approaches have been used for the pre-treatment step, e.g., autohydrolysis, acid hydrolysis, ammonia activation, kraft pulping, organic solvent pulping, hot water pre-treatment, ammonia percolation, lime pre-treatment, caustic soda pulping, or alkali peroxide pre-treatment. Early pre-treatment steps included grinding or milling the feedstock into a powder, which was then mixed with water to form a slurry.

More recently, solvent based pre-treatments, alkali pre-treatments, and acidic pre-treatments have also been described. PCT publication WO/2007/009463 to Holm Christensen describes an alternate pre-treatment, which does not involve the addition of acids, bases, or other chemicals. This pre-treatment process involves soaking the cellulosic material in water, conveying the cellulosic material through a heated and pressurized reactor, and pressing the cellulosic material to produce a fiber fraction and a liquid fraction. During the soaking step, approximately 2.5-3.5 kg of liquid per 1 kg of fiber is added, and is removed again during pressing. The overall pre-treatment process can take about 27 minutes.

Each pre-treatment technology has a different mechanism of action on the plant structure, inducing either physical and/or chemical modifications. However, the main objective of the pre-treatment is to provide accessibility of the plant material to the enzymes.

SUMMARY

The commercial viability of a hydrolysis process is dependent on the character of the feedstock provided to the hydrolysis unit. Typically, this requires that a feedstock is activated such that a significant portion (e.g., greater than 75%) of the cellulose and hemicellulose of the feedstock is accessible to hydrolysis enzymes. If such an activated feedstock is provided to an enzymatic hydrolysis unit, then at least 60%, preferably more than 75% and more preferably over 90% of the cellulose and hemicelluloses may be converted to monomeric sugars. This sugar rich process stream may subsequently be subjected to fermentation to produce an alcohol stream. The alcohol stream from the fermentation stage (i.e., the raw alcohol stream) may have an ethanol content of about 3-22% v/v, preferably about 5-15% and more preferably more about 8-12%.

An activated feedstock for enzymatic hydrolysis is preferably prepared by autohydrolysis, which is preferably conducted in a steam explosion reactor also known as a hydrolyzer, (also known as a digester). Autohydrolysis is a process of breaking down hemicellulose and cellulose by exposure to high temperatures, steam and pressure. When performed in the presence of an added acid, the reaction is known as acid hydrolysis.

During autohydrolysis, the degree of polymerization of cellulose may be reduced from about 10,000 to about 1,500-1,000. This process is preferably carried out above the glass transition temperature of lignin (120-160° C.). Depending upon the severity of the reaction, degradation products may be produced, such as furfural, hydroxyl-methylfurfural, formic acid, levulinic acid and other organic compounds.

During a steam explosion treatment (more commonly called autohydrolysis if no externally added catalyst), a cellulosic feedstock is subjected to elevated heat (e.g 180° C. to 220° C.) and pressure (e.g., 131 psig to 322 psig) optionally in the presence of suitable chemicals (e.g., organic/ and/or inorganic acids, ammonia, caustic soda, sulfur dioxide, solvents etc.) in a pressurized vessel. Preferably, external chemical addition is not utilized, in which case, the only catalyst that may be present may be acetic acid that is generated in situ. The treated cellulosic feedstock is then released from the pressurized vessel such that the pressure is rapidly reduced (e.g., 1 second or less). The biomass may exit the hydrolyzer into a reduced pressure, preferably atmospheric pressure and, more preferably into a vacuum. The rapid decrease in pressure results in the biomass separating into individual fibers or bundles of fibers. This step opens the fiber structure and increases the surface area. The lignin remains in the fiber along with cellulose and residual hemicellulose. Accordingly, the explosive release of pressure, combined with the high temperature and pressure treatment results in the physico-chemical modification of the cellulosic feedstock that is then suitable for feeding to an enzymatic hydrolysis unit.

In order for the steam explosion process to be able to produce an activated feedstock that is capable of producing such a sugar rich process stream, the temperature and moisture level of the cellulosic feedstock that is fed to a steam explosion reactor preferably is relatively uniform and preferably has a temperature from about 50 to about 70° C., and more preferably 50-65° C. and a moisture content from about 30 to 60 wt % (preferably 45 to about 55 wt %).

Without being limited by theory, it is believed that an unexpected increase in the conversion of the feedstock to fermentable sugars may be achieved if the moisture content of the feedstock fed to the steam explosion reactor is lower, provided that sufficient water is present for hydrolyzing and/or activating the feedstock. If the feedstock is too dry, then there may be insufficient water molecules present in the water and hence not all of the feedstock will be activated and/or hydrolyzed (i.e., the hydrolysis reaction/activation will not occur at all possible sites). Accordingly, it might be presumed that a substantial excess of water should be used to ensure water molecules are available at each hydrolysis/activation site. Surprisingly, it has been determined that if the cellulosic feedstock that is fed to a steam explosion reactor has an excess of moisture then a smaller percentage of the available sites of the feedstock are activated and/or hydrolyzed than would be expected. It is believed that this is due to the high moisture content acting as a barrier to heat transfer through the fiber structure. The external fiber reaches the process temperature far in advance to the internal fiber, hence resulting in very uneven heat transfer and the resulting uneven autohydrolysis reaction. Further, during the autohydrolysis process additional water may be provided to the process by way of direct injected steam in order to raise the fiber temperature from the inlet temperature to the outlet temperature of the reactor. If the inlet moisture content of the fiber is at saturation, then the additional water will be free water in the autohydrolysis reactor resulting in washing of the soluble hemicellulose from the fiber and causing subsequent accumulation of hemicellulose within the reactor. Over time, the accumulated hemicellulose will tend to break down to inhibitor compounds and deposit degraded sugars on the internal components of the reactor. These deposits will become an obstruction to the flow of the biomass.

It has also been determined that if the cellulosic feedstock that is fed to a hydrolyzer has a temperature that is too high, then some percentage of the hemicellulose sugars will be degraded to inhibitory compounds prior to starting the autohydrolysis reaction and further amounts during the autohydrolysis reaction itself. Conversely, if the fiber is too cold entering the hydrolyzer, the first one third to one half of the reactor vessel may act as a preheating device rather than as an autohydrolysis reactor, resulting in incomplete autohydrolysis. Accordingly, it is preferred to have very consistent fiber temperature year round as well as from night to day time operation, for the fiber that is fed to the hydrolyzer.

Alternately, and in addition, it is preferred that the fiber in the feedstock fed to the autohydrolysis unit have a relatively uniform temperature profile. For example, it is preferred that the core of the feedstock material have a temperature that is within 80%, more preferably 90%, most preferably 95% of the temperature of the exterior surface of the material. Accordingly, for example, if the temperature of the exterior surface of the material is from 50 to 70° C., then the temperature of the core of the material is preferably from 45 to 63° C.

It has also been determined that the fiber requires time for the moisture that is added to become equilibrated throughout the entire fiber particle. It has been determined that under laboratory conditions, it may take from 5 to 9 minutes to equilibrate the moisture content of the fiber. Under industrial conditions it will be longer. Preferably, the autohydrolysis reaction time in the vessel is typically about 5 to 6 minutes or less. It is preferred that the fiber in the feedstock fed to the autohydrolysis unit have a relatively uniform moisture profile. For example, it is preferred that the core of the blocks of material have a moisture content that is within 80%, more preferably 90%, most preferably 95% of the moisture content of the exterior surface of the material. Accordingly, for example, if the moisture content of the exterior surface of the material is from 45 to 55 wt %, then the moisture content of the core of the material is preferably from 40.5 to 49.5 wt %.

Accordingly, embodiments of the present invention relate to a cellulosic feedstock pre-treatment apparatus which mixes the feedstock, optionally with heating and/or moisture addition, to prepare the feedstock for hydrolysis, and a method of use thereof. Subsequent to this soaking or impregnation stage, it is preferred to subject the feedstock to an autohydrolysis reaction.

In one broad aspect, an apparatus for conveying a cellulosic feedstock is provided. The apparatus comprises an enclosed volume having a length along which the cellulosic feedstock is conveyed. The enclosed volume has a lower surface comprising a plurality of longitudinally extending portions. Each longitudinally extending portion has an inner surface that is arcuate in transverse section. A plurality of conveyance members are provided within the enclosed volume. Each conveyance member is associated with one of the inner surfaces and configured to sweep the one of the inner surfaces.

Embodiments in accordance with this broad aspect may be advantageous because the apparatus may convey the cellulosic material in a substantially continuous fashion, while preventing blockages from occurring, and preventing material from becoming stuck in the apparatus or having a residence time that is excessive. Furthermore, embodiments in accordance with this broad aspect may be advantageous because the enclosed volume may prevent the cellulosic material from drying out, and from losing heat. Further, embodiments in accordance with this broad aspect may allow the cellulosic material to be conveyed through the enclosed volume while being mixed. Accordingly, the temperature and moisture content of the cellulosic feedstock may be substantially homogenous throughout the feedstock. This cellulosic feedstock is preferably used for subsequent ethanol production. For example, the heated moistened feedstock may be subsequently subjected to hydrolysis, preferably autohydrolysis followed by enzymatic hydrolysis.

In some embodiments, each conveyance member comprises a longitudinally extending rotary shaft, and a conveying member (e.g., a plurality of paddles or a continuous screw on a shaft) extending outwardly from the shaft and in the case of discrete members such as paddles, staggered axially along the shaft.

In some embodiments, the conveying member and the lower surface are configured to maintain a space between the conveying member and the lower surface of less than 6.5 mm. In accordance with this embodiment, if the conveying member comprises a plurality of paddles, then the paddles and the lower surface are configured to maintain a space between a given paddle and the lower surface of less than 6.5 mm when the given paddle is adjacent the lower surface. The spacing may vary depending upon the size of the particulate matter in the feedstock. The larger the size of the particulate matter, the larger the spacing may be. Preferably, the spacing is less than the maximum particle size and, more preferably, less than the median particle size. For example, if each portion has a lower surface that is semi circular, the conveyance member associated with each portion may be configured to sweep the lower surface. As the shafts rotate, particulate matter will be continually moved through the chamber despite the lower surface of the apparatus having a smooth, continuous lower surface.

In some embodiments, the conveying member comprises a plurality of paddles each comprising a generally planar blade having a radial inner edge attached to stem, a radial outer edge opposite the radial inner edge, and opposing first and second side edges extending between the radial inner and outer edges, and the radial outer edge is curved to match an arc swept by the outer edge when the shaft rotates.

In some embodiments, each blade is canted, wherein the first side edge is axially nearer the outlet and rotationally trailing relative to a second side edge.

In some embodiments, the first side edge of one paddle axially overlaps the second side edge of a next adjacent paddle.

In some embodiments, adjacent shafts are spaced transversely apart from each other and are generally parallel and rotate in opposite directions.

In some embodiments, at least some of the paddles have an arcuate radial outer edge that is shaped to mate with at least one of the inner surfaces.

In some embodiments, each inner surface defines a first sector of a circle having a first radius and a radial outer edge of each paddle describes a second sector of a circle having a second radius as it rotates, and the second radius is essentially the same as the first radius of at least one of the inner surfaces.

In some embodiments, the paddles are staggered circumferentially along the shaft.

In some embodiments, the enclosed volume comprises an upper inner arcuate surface having first and second transversely opposed lower longitudinally extending sides, wherein one of the longitudinally extending portions has an upper outer side configured to merge with the first lower longitudinally extending side, and another of the longitudinally extending portions has an upper outer side configured to merge with the second lower longitudinally extending side.

In some embodiments, the longitudinally extending portions are positioned side-by-side.

In further embodiments, the apparatus may be configured to provide heat and/or moisture to the cellulosic feedstock, in order to maintain or raise the feedstock to a desired moisture content and temperature as it is conveyed, or to pre-treat the cellulosic feedstock by further moistening and heating the cellulosic feedstock.

In some such embodiments, the conveyance members have fluid injection ports. In further embodiments, each conveyance member comprises a longitudinally extending rotary shaft and the shaft comprises a fluid conduit extending longitudinally therethrough. In yet further embodiments, the shaft comprises a fluid conduit extending longitudinally therethrough and at least one of the stem and the paddles comprise injection ports.

In a further broad aspect, a method is provided for conveying a cellulosic feedstock. The method comprises providing a cellulosic feedstock being less than 100% saturated with moisture, preferably less than 50% moisture on a weight basis and more preferably less than 15 wt % (e.g., 5-15 wt %). Moisture content is the quantity of water contained in a material, and on a weight basis, is the weight of water in the material divided by the mass of the material. The cellulosic feedstock is introduced into a longitudinally extending enclosed volume, and conveyed longitudinally through the enclosed volume while being heated. The cellulosic feedstock is mixed as it is conveyed through the enclosed volume.

Embodiments in accordance with this broad aspect may be advantageous because the heating and mixing of the feedstock may produce a more uniform temperature and moisture content of the feedstock thereby enhancing downstream hydrolysis of the feedstock. Furthermore, the process permits the heating and mixing of the feedstock while requiring relatively small amounts of heat and energy. Accordingly, the process may prevent overheating of the fibers in the feedstock, thereby preventing degradation of the fibers.

In some embodiments, the method further comprises operating the enclosed volume at less then 100% fill volume, whereby an upper portion of the enclosed volume is open. Preferably, the process is operated such that the enclosed volume may operate at a low fill factor, for example from 10 to 50 and preferably about 30%.

In some embodiments, the step of mixing the cellulosic feedstock comprises projecting a portion of the cellulosic feedstock into the upper open portion of the enclosed volume while conveying the cellulosic feedstock longitudinally through the enclosed volume.

In some embodiments, the enclosed volume has a plurality of longitudinally extending portions, each portion has an inner surface that is arcuate in transverse section, and the method further comprises conveying the cellulosic feedstock longitudinally along each inner surface.

In some embodiments, the enclosed volume has a lower surface, and the method further comprises sweeping a lower surface to convey the cellulosic feedstock through the enclosed volume.

In some embodiments, the lower surface comprises a plurality of longitudinally extending portions, and the method further comprises rotating a plurality of conveyance members to pass conveying members of each conveyance member proximate one of the inner surfaces such that conveying members of each conveyance member contact the cellulosic feedstock and urge the cellulosic feedstock along the length of each inner surface.

In some embodiments, the method further comprises maintaining a residence time of less than 10 minutes.

In some embodiments, the feedstock is mixed such that the feedstock has a generally uniform moisture content of 30 to 60% by weight, preferably 45% to 55% by weight, upon exiting the enclosed volume.

In some embodiments, the method further comprises conveying the cellulosic feedstock downwardly to a holding tank upon exiting the enclosed volume.

In some embodiments, the method further comprises subsequently subjecting the cellulosic feedstock to a downstream hydrolysis process, preferably autohydrolysis followed by enzymatic hydrolysis.

BRIEF DESCRIPTION OF THE DRAWINGS

These and other advantages of the present invention will be more fully and particularly understood in connection with the following description of the preferred embodiments of the invention in which:

FIG. 7A is a perspective illustration of an embodiment of a paddle of the present invention;

FIG. 7B is a front plan view of the paddle of FIG. 7A;

FIG. 7C is a side plan view of the paddle of FIG. 7A;

FIG. 7D is a top plan view of the paddle of FIG. 7B;

FIG. 8A is a partial perspective illustration of an embodiment of a conveyance member of the present invention, wherein the paddle of the conveyance member comprises injection ports;

FIG. 8B is a partial front plan view of the paddle of FIG. 8A;

FIG. 8C is a partial side plan view of the paddle of FIG. 8A; and,

FIG. 8D is a transverse cross-section taken along line D-D in FIG. 8A.

DETAILED DESCRIPTION

Figure 1:
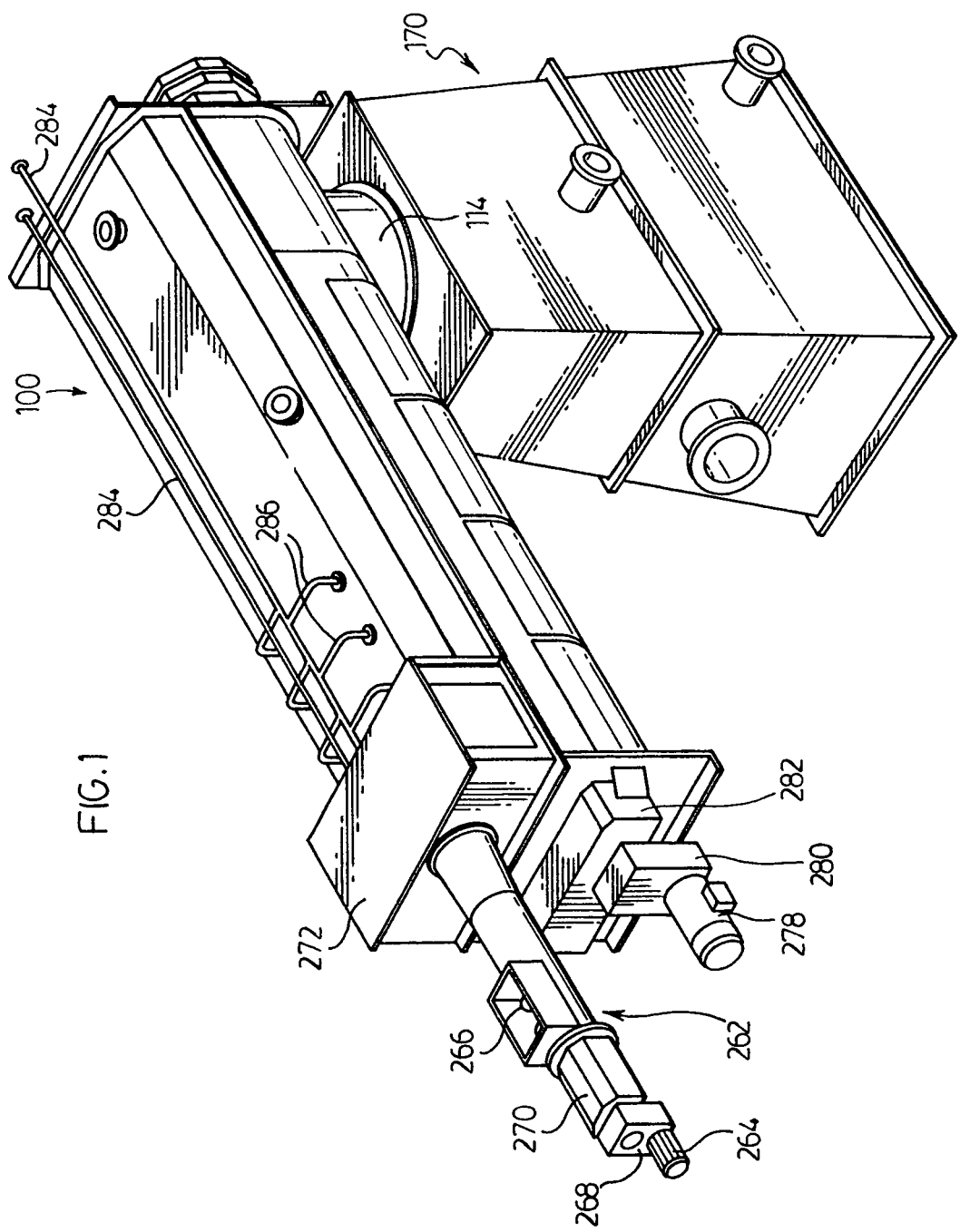
FIG. 1 is a perspective illustration of an embodiment of an apparatus of the present invention.

Embodiments of the present invention provide a method and apparatus for treating a cellulosic feedstock that may be used for subsequent ethanol production. The method and apparatus of the preferred embodiment serve to mix the feedstock, and optionally to heat and/or moisten the cellulosic feedstock, to obtain a relatively uniform temperature and moisture level or profile of the feedstock, while reducing, and preferably essentially preventing, the charring or other degradation of the cellulose and hemicellulose during this heating stage. Accordingly, the method and apparatus provide a cellulosic feedstock, which is suitable for the production of a fermentation precursor stream. The cellulosic feedstock may be subsequently treated to liberate sugars in the cellulose and hemicellulose and produce a sugar stream that may then be subjected to fermentation to obtain a high yield alcohol stream.

An embodiment of an apparatus 100 of the present invention is shown in FIGS. 1-7. In this embodiment, apparatus 100 is configured to convey a cellulosic feedstock, for example from a holding tank or a moisture addition determination stage wherein the amount of moisture in the feedstock is determined and the amount of moisture required to obtain a predetermined moisture content is determined, to an autohydrolysis reactor. An alternate embodiment of apparatus 100 of the present invention is shown in FIG. 8. In this embodiment, apparatus 100 is further configured to convey the cellulosic feedstock while providing heat and/or moisture to the cellulosic feedstock, for example to maintain a desired temperature and moisture content of the cellulosic feedstock, by providing moisture, preferably heated moisture, to the central portion of the apparatus.

It will be appreciated that although the method is described with reference to apparatus 100 and vice versa, the method may be carried out with an alternate apparatus, and apparatus 100 may be used according to an alternate method. Furthermore, although the method is described as a continuous process, it will be appreciated that the method may be carried out as a semi-continuous or batch process.

The cellulosic feedstock treated according to the method and/or utilizing apparatus 100 is preferably a lignocellulosic feedstock. A lignocellulosic feedstock is derived from plant materials. As used herein, a "lignocellulosic feedstock" refers to plant fiber containing cellulose, hemicellulose and lignin. In some embodiments, the feedstock may be derived from trees, preferably deciduous trees such as poplar (e.g., wood chips). Alternately or in addition, the feedstock may also be derived from agricultural residues such as but not limited to corn stover, wheat straw, barley straw, rice straw, switchgrass, sorghum, bagasse, rice hulls and/or corn cobs. Preferably, the lignocellulosic feedstock comprises agricultural residues and wood biomass, more preferably wood biomass and most preferably deciduous. The applicants contemplate other sources of plant materials comprising cellulose, hemicellulose and/or lignin, such as algae, for use in deriving cellulosic feedstocks and any of those may be used.

The lignocellulosic feedstock is preferably cleaned, e.g., to remove ash, silica, metal strapping (e.g., from agricultural products), stones and dirt. The size of the components of the lignocellulosic feedstock may also be reduced. The size of the components of the feedstock may be from about 0.05 to about 2 inches, preferably from about 0.1 to about 1 inch, and more preferably from about 0.125 to about 0.5 inches in length. For example, the cellulosic feedstock may comprise fibers, e.g., chopped straw, of a length of between about 4 mm and about 7 mm. Any process machinery that is able to crush, grind or otherwise decrease the particle size may be utilized.

Generally, when the cellulosic feedstock is provided, it will have an initial or starting moisture content. The initial moisture content may depend on numerous factors, such as the nature of the cellulosic feedstock, and any upstream storage conditions. In some embodiments, the initial moisture content is less than about 15 wt % and, preferably, from 5-15 wt %. In some embodiments, at least some moisture may be provided in advance of the apparatus. If no moisture is added in apparatus 100, then the initial moisture content may be from 40-50 wt %.

Referring to FIGS. 1-4, apparatus 100 comprises an enclosed volume or chamber 102, which has a length L, along which the cellulosic feedstock is conveyed. Length L may vary depending on the particular embodiment, and in some embodiments may be between about 10 ft and about 30 ft.

In some embodiments, an impregnator feeder 262, namely a feeder that conveys feedstock into chamber 102, is preferably positioned upstream of mixing or impregnation chamber 102. Feeder 262 may be of any design. Preferably, feeder 262 is of a design that inhibits, and preferably prevents, the flow of moisture upstream of feeder 262. For example, a rotating valve or the like may be provided to segment such upstream flow. Preferably impregnation feeder is a screw feeder comprising a motor 264 drivingly connected to a screw or auger 266 positioned below an inlet, such as via a transmission or gear reduction assembly provided in housing 268. The shaft on which screw 266 is provided may be rotatably mounted in housing 270 such that auger 266 is a cantilevered plug screw conveyor. Accordingly, feeder 262 produces a plug of material that prevents upstream migration of moisture. The plug may be conveyed into inlet housing 272 that is mounted, e.g., to outer wall 105 and positioned above inlet 101 to chamber 102. The feedstock may then pass downwardly into chamber 102.

In the embodiment shown, chamber 102 is defined by a shell, which is preferably provided with a heating jacket 160. Accordingly, the shell preferably comprises an inner wall 104 having an inner surface 109 and a spaced apart outer wall 105 defining a volume 162 therebetween. Accordingly, chamber 102 may be a double walled chamber having a volume 162 through which a heated fluid may be passed from an inlet to an outlet. Accordingly, the heated fluid circulates within enclosure 162, and provides heat to the cellulosic feedstock. The heated fluid may be water, for example, or steam. For example, if steam is not used to provide heat to the fibers in the treatment chamber, but water at, e.g., 50-60° C. is used, the feedstock will be heated but will not be raised to a temperature at which degradation may occur. Preferably, the temperature of water in the heating jacket is from 70 to 90, preferably from 75 to 85° C. Any heating jacket or the like known in the art may be used. Alternately, a heating jacket need not be used or may only surround a portion of the inner wall 104. In such a case, inner wall may be the only wall surrounding volume 102.

In the embodiment shown, the cellulosic material is preferably conveyed towards a holding tank 170 after exiting chamber 102. Apparatus 100 comprises at least one inlet 101, and at least one outlet 103, positioned at opposed ends of volume 102. Preferably inlet 101 is defined in upper surface 108, and outlet 103 is defined in the lower surface, such that cellulosic material may be deposited into enclosed volume 102 via inlet 101, be conveyed along length L of enclosed volume 102, and drop out of enclosed volume 102 via outlet 103 and travel downwardly to holding tank 170, such as via passage 114.

Chamber 102 has a lower surface that is configured such that conveyance members 130 may sweep adjacent all of, or much of, the lower wall to reduce the likelihood of material having an increased residence time by not being conveyed through chamber 102. Accordingly, the lower surface and the conveyance member are configured so as to sweep the lower surface. In the exemplified embodiment, the lower surface is scallop shaped and the conveyance member has paddles that are positioned and configured to sweep the trough of each scallop shaped surface. Other shapes may be used provided that one or more conveyance members has a configuration that is compatible with the shape of the lower surface.

Figure 5B:
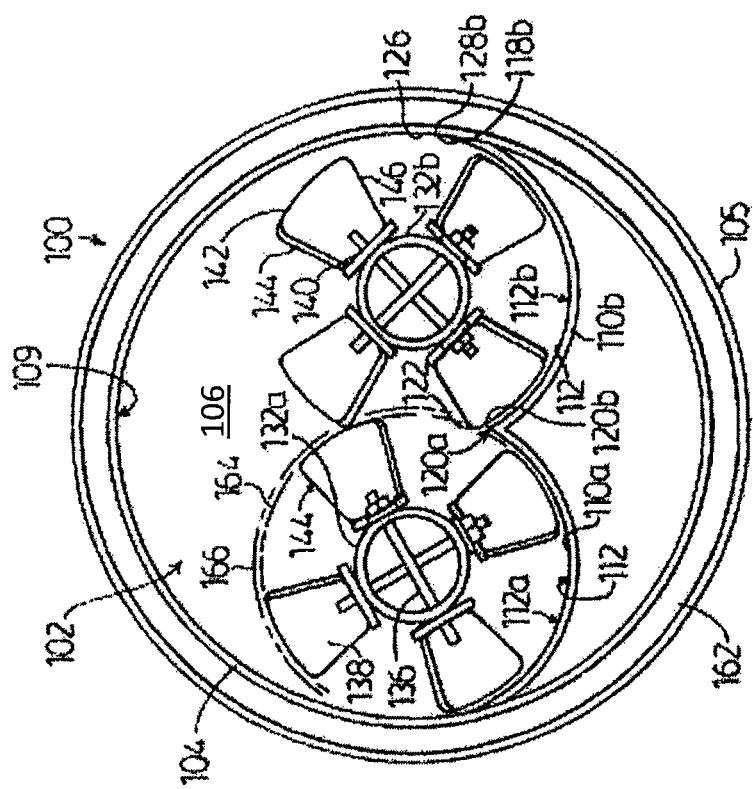
FIGS. 5A and 5B are transverse cross-sections taken along line 5-5 in FIG. 2, showing various rotational positions of an embodiment of a conveyance member of the present invention.
Figure 5A:
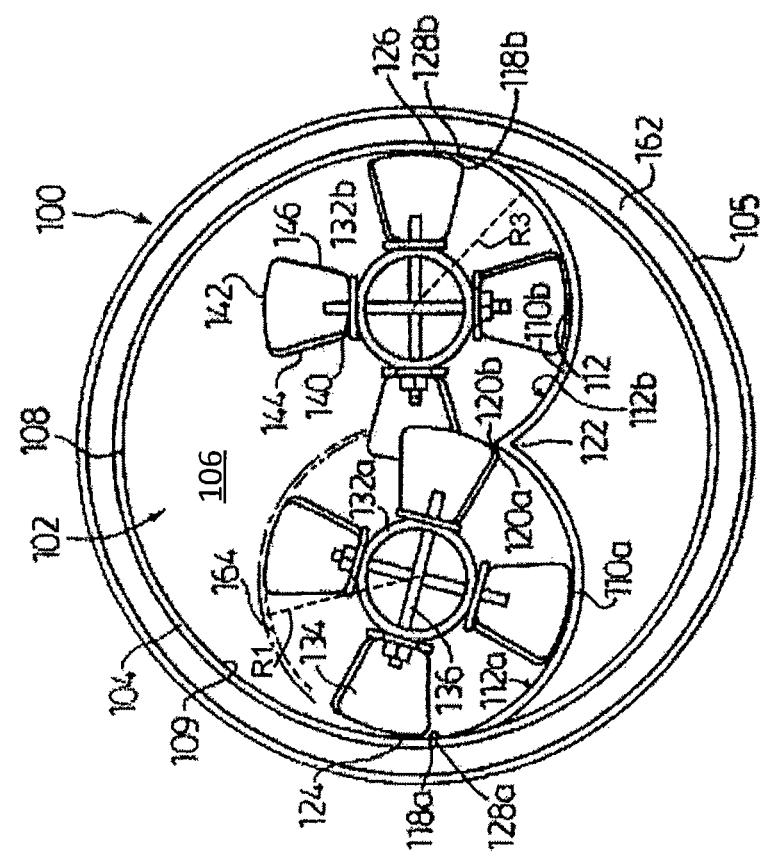

Referring still to FIGS. 5A and 5B, enclosed volume 102 is exemplified as a lower surface comprising a plurality of longitudinally extending portions 110 and an upper surface 108. Each portion may be a wall section that is added to the inside of inner wall 104. As exemplified, lower surface comprises two portions, 110a, and 110b. In other embodiments, lower surface may comprise greater than two portions. For example, lower surface may comprise three portions. Portions 110a, 110b each have an inner surface 112a, 112b that is preferably arcuate in transverse section. That is, when viewed in transverse section in FIGS. 5A and 5B, the inner surface of each portion 110a, 110b defines an arc. In the embodiments shown, each arc is a circular arc (i.e., defines a sector of a circle), and the radius R1 of each arc is preferably essentially identical. However, in alternate embodiments, one or more of the arcs may be an elliptical arc, and the arcs may have non-identical radii.

Each of the inner surfaces 112a, 112b has an upper outer side 118a, 118b, and an upper inner side 120a, 120b. In the embodiments shown, the upper inner sides 120a, 120b meet at an apex 122. That is, portions 110a and 110b are side-by-side. In alternate embodiments, the upper inner sides 120a, 120b may be spaced apart and the lower surface of chamber 102 may further comprise a third portion extending between upper inner sides 120a, 120b. An advantage of providing an apex 122 is that feedstock will tend not to be retained on the lower surface between adjacent the arcs.

As exemplified in FIGS. 5A and 5B, upper surface 108 comprises a longitudinally extending wall having an inner surface 109 that is arcuate (e.g., semi cylindrical). In alternate embodiments, upper surface 108 may have an inner surface that, for example, comprises a plurality of longitudinally extending portions (e.g., be scallop shaped similar to portions 110) or may have an inner surface that is flat in transverse section.

As exemplified in FIGS. 5A and 5B, inner surface 109 has first transversely opposed lower side 124 and second transversely opposed lower side 126, which are longitudinally extending. The first side 124 of upper surface 108 meets or merges with upper outer side 118a at point 128a, and the second side 126 of upper surface 108 meets or merges with upper outer side 118b at point 128b. In the embodiments shown, the sides meet at the portions denoted by reference numerals 128a and 128b in a substantially smooth fashion. However in alternate embodiments, the sides may meet in a substantially abrupt fashion.

Apparatus 100 further comprises one or more conveyance members 130 which are provided within enclosed volume 102. Preferably, a conveyance member is associated with each portion 110 of the lower surface. As exemplified, a conveyance member 130 is centered above each inner surface 112 of a portion 110 (e.g., the longitudinal axis of each conveyance member is coaxial with the longitudinal axis of the centre of a circle described by its associated portion 110). Accordingly, in the embodiments shown, apparatus 100 comprises a first conveyance member 130a associated with inner surface 112a, and a second conveyance member 130b associated with inner surface 112b. In alternate embodiments apparatus 100 may comprise greater than two conveyance members, depending on the configuration of lower surface 112. Each conveyance member 130 is configured to convey cellulosic material longitudinally through volume 102 by sweeping its respective inner surface 112. That is, each conveyance member 130 is configured such that at least a portion thereof passes over an inner surface 112 in a continuous motion to push the cellulosic material forwardly (i.e., in a direction away from inlet 101 and towards outlet 103).

Figure 4:
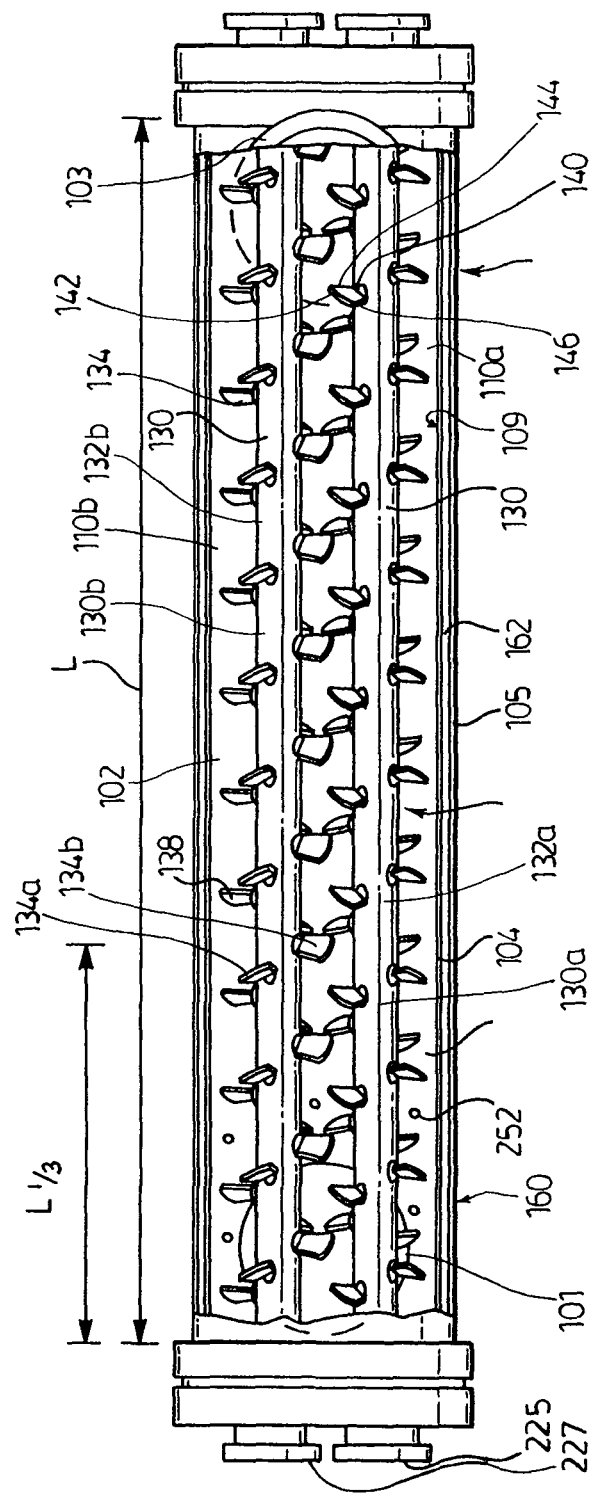
FIG. 4 is a top view of the apparatus of FIG. 1, with the upper portion of the apparatus removed, showing the interior of the apparatus.
Figure 6:
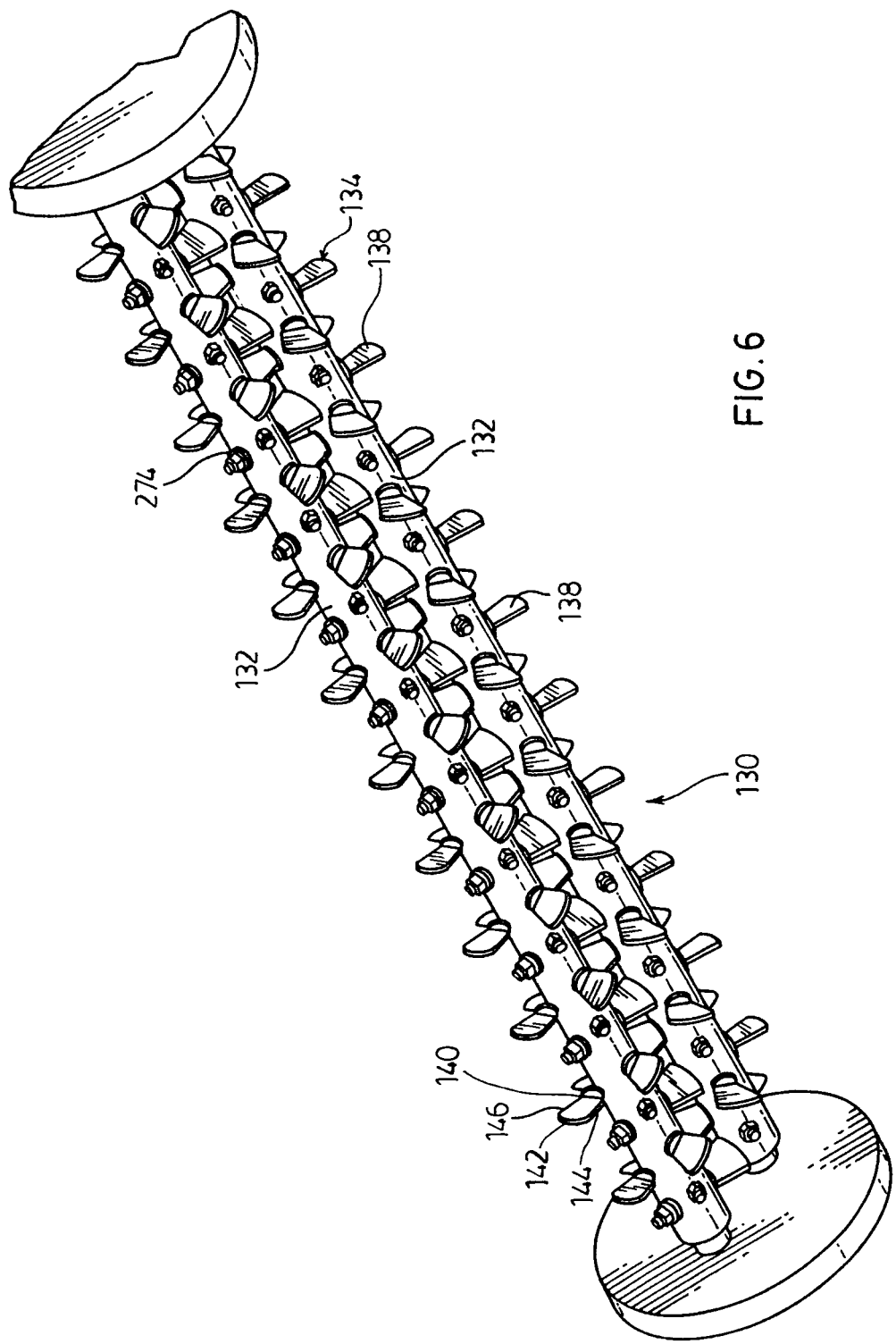
FIG. 6 is a perspective illustration of an embodiment of a conveyance member of the present invention.

Referring to FIGS. 4-6, in the embodiments shown, in order to sweep its respective inner surface, each conveyance member 130 comprises a longitudinally extending rotary shaft 132a, 132b. The rotary shafts 132a, 132b are adjacent and spaced transversely apart from each other, and are generally parallel. One or more conveying members, such as a plurality of paddles 134, extend outwardly from each shaft 132. As exemplified in FIGS. 7A-7D, the paddles each comprise a stem 136, which is coupled to the rotary shaft, and a generally planar blade 138, which extends from and is attached to each stem 136. Each blade 138 comprises a radial inner edge 140 which is attached to a stem 136, a radial outer edge 142 opposite the radial inner edge, and opposing first side edge 144 and second side edge 146 extending between the inner and outer edges 140, 142.

Preferably, as exemplified in FIG. 4, the paddles 134 are staggered axially and circumferentially along each shaft 132, such that they are generally arranged helically around each shaft 132. In other words, a helix would be defined if the radial outer edge 142 of paddles were connected by a line extending from the inlet end of a rotary shaft to the outlet end thereof. Accordingly, helically adjacent paddles 134, for example paddles 134a and 134b, extend from the shaft at different angular positions around the shaft axis, as can be seen in FIG. 4.

Preferable, each blade 138 is canted, such that a first side edge 144 is axially nearer outlet 103 and rotationally trailing relative to a second side edge 146.

Additionally, when viewed axially along the length of a rotary shaft, the first side edge 144 of one paddle 134a axially overlaps the second side 146 edge of an adjacent paddle 134b.

Accordingly when the rotary shafts 132 rotate, paddles 134 pass over inner surfaces 112 in a continuous motion to push the cellulosic material forwardly. An advantage of the exemplified design is that the outer radial edges of the blades are configured to travel a generally consistent distance above longitudinally extending portions 110, thereby being able to effectively sweep longitudinally extending portions 110.

In alternate embodiments, the paddles may be otherwise configured. For example, they may not be canted, and may be wedge shaped. Additionally, they may, for example, be arranged in a grid around shaft 132, rather than in a helix. It will be appreciated that in a particularly preferred embodiment, the paddles are arranged to define a helix, the blades are canted and the first side edge of one paddle axially overlaps the second side edge of a next adjacent paddle. However, these features may be used in any particular sub-combination.

Figure 2:
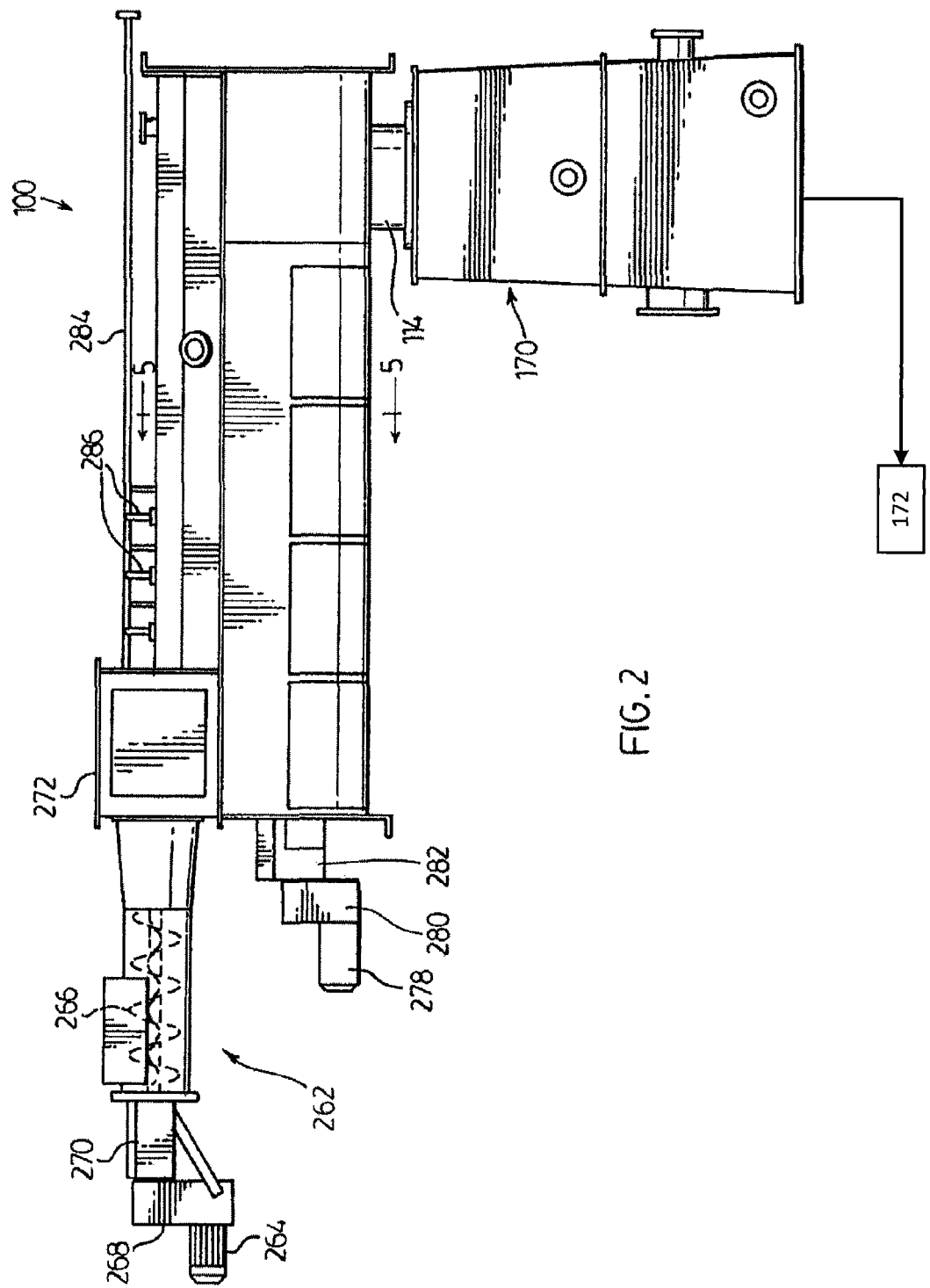
FIG. 2 is a front plan view of the apparatus of FIG. 1.
Figure 3:
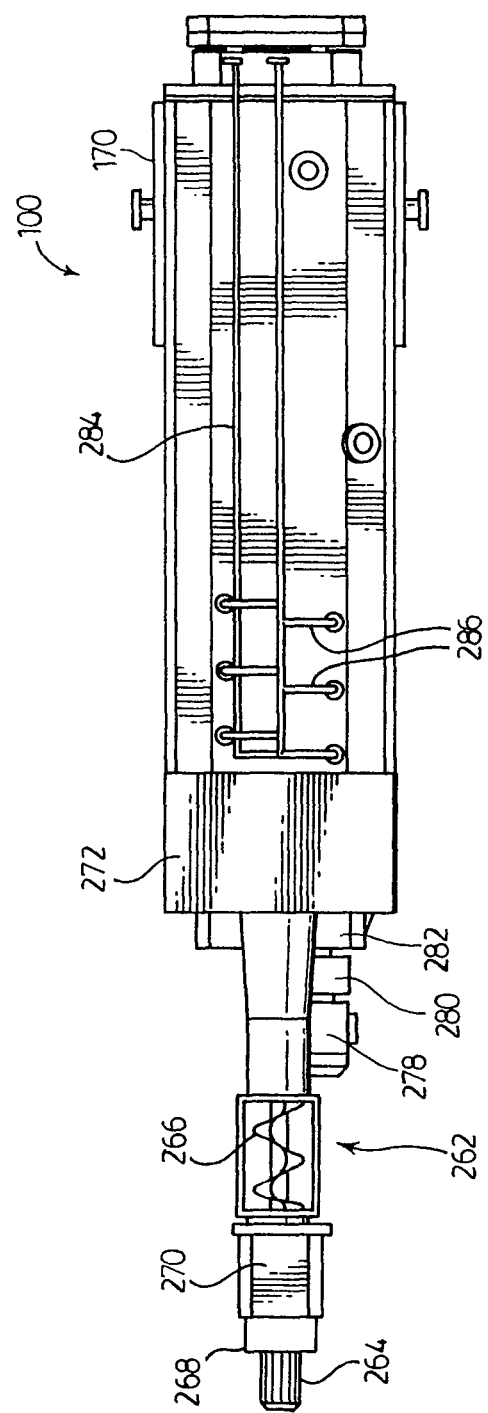
FIG. 3 is a top plan view of the apparatus of FIG. 1.

As exemplified in FIGS. 1-3, conveyance members 130 are rotatably mounted in chamber 102 and are drivenly connected to a motor 278. As exemplified, motor 278 is drivingly connected to conveyance members 130 via a transmission or gear reduction assembly provided in housing 280. The gear reduction assembly may be drivingly connected to ends 225, 227 of conveyance members 130 that are positioned inside housing 282. However, conveyance members 130 may be rotatably mounted by any means known in the art.

Rotary shafts 132a, 132b are preferably configured to rotate in opposite direction, but may rotate in the same direction.

It will be appreciated that, in alternate embodiments, conveyance members 130 may be otherwise configured. For example, conveyance members 130 may comprise an auger such that the conveying member is a continuous or discontinuous screw mounted on a shaft, which extends along enclosed volume 102, and which is rotated to urge the cellulosic feedstock through volume 102 and sweep inner surfaces 112.

In accordance with this particularly preferred aspect, paddles 134 and portion 110 are configured such that when a given paddle is adjacent and passing over surface 112, a substantially constant distance is maintained between the outer edge 142 of the paddle 134, and surface 112. Such embodiments may aid in ensuring that the cellulosic material is urged forwardly at a substantially constant rate, and that the cellulosic material is not retained in the chamber.

For example, in the embodiments shown, the outer edge 142 of each blade 138 is curved or arcuate in shape (see for example FIG. 7B), and the curve matches an arc swept or defined by the outer edge 142 as the shafts 132 rotate. That is, outer edge 142 of each blade 138 is curved to define a sector of a circle having a radius R2. When shafts 132 rotate, the outer edge 142 of each blade 138 will describe a sector of a circle 164 having a radius R3. In embodiments wherein blades 138 are not canted, for example wherein blades 138 are wedge shaped, R3 will equal R2. In embodiments wherein blades 138 are canted, R3 will be less than R2.

Further, longitudinally extending portion 110 is configured such that the inner surface 112 defines an arc of a circle 166 of radius R1 in transverse section. The blades are configured such that R3 is less than, e.g., about 6.5 mm smaller than R1. Accordingly, when shafts 132 rotate, and a given paddle 134 is adjacent and passing over a lower inner surface 112, a substantially constant distance is maintained between the outer edge 142 of the blade 138 of the paddle 134, and the inner surface 112. Preferably, R1 and R3 are essentially the same (i.e. R3 is less than R1 by a small tolerance factor), such that when a given paddle 134 is adjacent and passing over a lower inner surface 112, outer edge 142 and inner surface 112 remain in close proximity. Such embodiments may aid in ensuring that the cellulosic material is urged forwardly at a substantially constant rate, and that the cellulosic material does not get stuck in the chamber. The spacing between radial outer edge 142 and the arc defined by surface 112 may be from 5 mm to 10 mm. The spacing may vary depending upon the size of the particulate matter in the feedstock. The larger the size of the particulate matter, the larger the spacing may be. Preferably, the spacing is less than the maximum particle size and, more preferably, less than the median particle size. Accordingly, as the shafts rotate, particulate matter will be continually moved through the chamber. Further, if longitudinally extending portions 110 are heated, then the particulate matter will be inhibited from staying in the same location and being possibly overheated such that cellulose or hemicellulose is degraded by heat.

Preferably, as exemplified in the embodiments shown in FIGS. 1 to 7, apparatus 100 is further configured to mix the cellulosic material as it is conveyed. That is, if rotary shafts 132 are operated at a high enough speed, for example about 55 rpm, blades 138 of paddles 134 will not only push cellulosic material along surfaces 112, but will also project cellulosic material upwardly, such that it intermingles with cellulosic material located forwardly or rearwardly of it within enclosed volume 102.

It will be appreciated that the conveyance member 130 preferably rotates at from 40 to 150 and, more preferably, about 45 to 75 rpm. Alternately, or in addition, the chamber may operate at a low fill factor, for example from 10 to 50 and preferably about 15 to 30%. Accordingly, a majority of the volume in chamber 102 may be filled with air. For example, if the fill factor is 30%, then only 30% of the volume of chamber 102 is filled with feedstock, the rest being filled with preferably air. As the conveyance member rotates, preferably at a relatively high speed, the feedstock will be thrown up into the empty upper portion of chamber 102 thereby mixing the feedstock to provide a more uniform distribution of heat and/or moisture throughout the feedstock. It will be appreciated that the use of a high rotational speed, combined with a low fill factor permits the use of a higher temperature in the heating jacket and/or in the temperature of the moisture provided to the feedstock in the chamber with reduced risk of heat degradation of the feedstock.

Preferably the air in chamber 102 is at a temperature of about 60 to 70° C. and about saturated.

In some embodiments, apparatus 100 is further configured to treat the cellulosic material as it is conveyed through enclosed volume 102. For example, apparatus 100 may be configured to heat, and/or moisten the cellulosic material as it is conveyed through enclosed volume 102.

For example, referring to FIGS. 8A-8D, an alternate embodiment of conveyance members 130 is shown. In this embodiment, conveyance members 130 comprise fluid injection ports, for adding moisture to the cellulosic material. In the embodiments shown, injection ports 252 are defined in blades 138 of paddles 134; however, in alternate embodiments, injection ports 252 may alternately or in addition be provided in stems 136 and/or in shafts 132. As shown, injection ports 252 extend inwardly from an outer surface of blades 138, and are in fluid communication with one or more paddle ducts 152 provided within paddles 134. The one or more paddle ducts 152 are in fluid communication with a fluid conduit 256, extending through shafts 132, for example via ports 258 provided in stem 136. Fluid conduit 256 is in fluid communication with a moisture source (not shown), for example at ends 225, 227 of shafts 132. Accordingly, as the conveyance member rotates moisture, may be introduced into volume 102 by passing from a moisture source into fluid conduit 256, through ports 258 in stem 136, through passage 254 and out of ports 252 in blades 138.

In alternate embodiments (not shown), the injection ports 252 may additionally or alternately be provided in lower surface 106 and/or upper surface 108 and/or in the outer wall of shafts 132. For example, in some embodiments, injection ports 252 are provided along the entire length L of chamber 102. In other embodiments, moisture injection ports 252 are preferably provided only in an upstream portion of chamber 102, preferably in the upstream half of the length L of chamber 102 and, more preferably in the first or upstream third $L_{1/3}$ of the length L of chamber 102 (see FIG. 4). For example, as exemplified in FIG. 1, a plurality of injection ports may be provided in the upper portion of chamber 102. As shown therein, one or more conduits 284 may convey water to a plurality of branch conduits 286 extending to different locations on the upper portion of chamber 102. The end of these conduits are in fluid flow communication with the interior of chamber 102, via a moisture addition member such as a nozzle or an open ended pipe or the like. As exemplified, six ports are provided. However, additional or fewer ports may be used. Accordingly, moisture injection ports may additionally or alternately be provided in the wall of chamber 102. That is, injection ports 252 may extend through inner wall 104.

The moisture may be added to the cellulosic material as liquid water, or may alternately be added as steam. Additionally, the water may not be pure water, and may comprise additional components. For example, one or more catalysts, including but not limited to mineral and organic acids, bases such as sodium hydroxide, organic solvents, and oxidizing agents such as hydrogen peroxide, may be added with the water.

Alternately, or in addition, in further embodiments as discussed, a heating jacket 160 may be provided. The heating jacket may be configured to heat upper surface 108 and/or lower surface (portions 110). It is preferred not to use steam since steam may result in the overheating of the cellulose and hemicellulose, causing degradation thereof. However, if the particularly preferred design exemplified herein is used, then higher temperatures may be used with reduced risk of degradation of the feedstock.

Alternately, or in addition, in other embodiments, the cellulosic feedstock may be heated by circulating steam in the conveyance member 130, for example, in paddles 134. In such embodiments the ports 252 are not provided.

Alternately, or in addition, in other embodiments, the cellulosic feedstock may be heated directly. For example, if moisture is being added to the celluosic material, heated water or steam may be added as part of the moisture. For example, water may be at a temperature of 50 to 75° C. and preferably 65 to 70° C.

Blade 138 may be secured to one end of stem 136 by any means known in the art, such as welding, or mechanical affixation members such as rivets, or screws. The other end of stem 136 may be provided with a screw thread 276 on which bolt 274 may be received. Stem 136 may be secured to shaft 132 such as by extending transversely through shaft 132 from one side to the other and bolt 274 secured thereon. Suitable packing, gaskets or the like may be provided to limit or prevent moisture leaking out of shaft 132 past stem 136. Stem 136 may be provided with one or more openings 258 in fluid communication with volume 256 inside shaft 132. Accordingly, moisture may flow through shaft 132, through passage 254 in stem 136 to paddle 134 and out through ports 252 into chamber 102. However, paddles 134 may be directly secured to shafts 132 or may be secured by any other means known in the art.

An embodiment of a method of the present invention will presently be described. Although the method will be described with reference to apparatus 100, it will be appreciated that the method may utilize an alternate apparatus, and the method is not limited to use with a particular apparatus.

The method serves to at least mix, and preferably to also heat and mix or moisten and mix, and more preferably to mix, heat and moisten the cellulosic feedstock while it is conveyed. The method may serve to maintain the temperature and/or moisture content of the cellulosic feedstock, or to pretreat the cellulosic feedstock to render the cellulose of the feedstock ready for a downstream process such as one or more of autohydrolysis, enzymatic hydrolysis, and subsequent ethanol production. Such further pre-treatment processes may include incubation at an elevated temperature, for example in holding tank 170, shown hereinabove.

A cellulosic feedstock being less than 100% saturated with moisture, preferably less than 50% moisture on a weight basis is introduced into a longitudinally extending volume, and is conveyed through the longitudinally extending volume while heating the cellulosic feedstock.

For example, in order to introduce the cellulosic feedstock into a longitudinally extending volume, the cellulosic feedstock may be deposited into inlet 101 of apparatus 100. Preferably, the cellulosic feedstock is introduced into enclosed volume 102 of apparatus 100 such that the enclosed volume 102 is operated at less than 100% fill volume. Preferably at least half of the volume 102 is left empty. That is, the rate at which the cellulosic feedstock is introduced into enclosed volume 102 is preferably selected such that an upper portion 106 of enclosed volume 102 is open during the operation of apparatus 100.

After being introduced into the longitudinally extending volume, the cellulosic feedstock is conveyed through the longitudinally extending volume. For example, in embodiments wherein apparatus 100 is utilized, the cellulosic feedstock is conveyed along the length of volume 102. In such embodiments, wherein apparatus 100 comprises longitudinally extending portions 110 having arcuate inner surfaces 112, arcuate inner surfaces 112 are preferably swept as feedstock is conveyed upwardly into the empty portion of the volume to enhance mixing and heat transfer. In other embodiments, the cellulosic feedstock may be mixed in another manner, for example by agitating a portion of the enclosed volume.

Accordingly, in some embodiments, the cellulosic feedstock is conveyed by sweeping a lower surface of the enclosed volume. For example, in embodiments wherein apparatus 100 is utilized, conveyance members 130a and 130b may be rotated to pass paddles 134 proximate inner surfaces 112a and 112b in a continuous motion to contact the cellulosic feedstock and urge the cellulosic feedstock along the length of each inner surface 112.

While the cellulosic feedstock is conveyed through the enclosed volume, it is preferably heated. In some embodiments, the cellulosic feedstock is heated to between about 50° C. to about 70° C. as it travels through the volume. That is the temperature of the feedstock is between about 50° C. to about 70° C. when it exits the enclosed volume. Preferably, the cellulosic feedstock is provided to the enclosed volume at less than about 30° C., and is heated to at least about 65° C. as it travels through the volume.

The cellulosic feedstock may be heated in a variety of ways. In some embodiments, wherein apparatus 100 is utilized, the feedstock may be heated by heating a surface of enclosed volume 102, a portion of conveyance members 130, and/or by providing heated water to the cellulosic feedstock.

The residence time of the cellulosic feedstock in the enclosed volume may vary. In some embodiments, the residence time may be less than about 10 minutes.

When the cellulosic feedstock exits the enclosed volume, it may be directed either directly or indirectly to a downstream hydrolysis preferably, an autohydrolysis process. For example, the cellulosic feedstock may be directed to a holding tank, for example holding tank 170 shown in FIGS. 1 and 2, such that it may be held at an elevated temperature to further pre-treat the cellulosic feedstock, and from the holding tank to a hydrolysis reactor 172 or an autohydrolysis reactor.

It will be appreciated that certain features of the invention, which are, for clarity, described in the context of separate embodiments or separate aspects, may also be provided in combination in a single embodiment. Conversely, various features of the invention, which are, for brevity, described in the context of a single embodiment or aspect, may also be provided separately or in any suitable sub-combination.

Although the invention has been described in conjunction with specific embodiments thereof, if is evident that many alternatives, modifications and variations will be apparent to those skilled in the art. Accordingly, it is intended to embrace all such alternatives, modifications and variations that fall within the spirit and broad scope of the appended claims. In addition, citation or identification of any reference in this application shall not be construed as an admission that such reference is available as prior art to the present invention.

We claim:

1. An apparatus for conveying a cellulosic feedstock, the apparatus comprising:
    (a) a feeder for conveying the cellulosic feedstock into an inlet housing positioned above an inlet of an enclosed volume;
    (b) the enclosed volume having a length along which the cellulosic feedstock is conveyed from the inlet located proximate to one end of the enclosed volume to an outlet proximate to an opposed end of the enclosed volume, the enclosed volume having:
        (i) an upper inner arcuate surface having longitudinally extending first and second transversely opposed lower sides;
        (ii) one or more conduits for conveying moisture to a plurality of fluid injection ports located in the upper portion of the enclosed volume for adding moisture to the cellulosic feedstock; and
        (iii) a lower surface comprising a plurality of longitudinally extending portions, each portion having an inner surface that is arcuate in transverse section;
        wherein one of the longitudinally extending portions has an upper outer side that merges with the first lower longitudinally extending side without a discontinuity, and another of the longitudinally extending portions has an upper outer side that merges with the second lower longitudinally extending side without a discontinuity; and
    (c) a plurality of conveyance members provided within the enclosed volume, each conveyance member being associated with one of the inner surfaces and configured to sweep the one of the inner surfaces, each conveyance member comprising a longitudinally extending rotary shaft, and a conveying member extending outwardly from the shaft, the conveying member including a plurality of paddles each having a generally planar blade having curved radial outer edge, the paddles being continuously staggered circumferentially along the shaft, wherein the conveying member on one of the conveyance members transversely overlaps the conveying member on another one of the conveyance members and the conveying members are spaced from the upper surface whereby the enclosed volume has an upper portion devoid of the conveying members,
    wherein the feeder is designed to produce a plug of cellulosic material that inhibits the flow of moisture from the enclosed volume upstream of the feeder.

2. The apparatus of claim 1, wherein the conveying member and the lower surface are configured to maintain a space between the conveying member and the lower surface of less than 6.5 mm.

3. The apparatus of claim 1, wherein each paddle further includes a stem, each blade has a radial inner edge opposite the radial outer edge, and the radial outer edge of each blade is curved to match an arc swept by the outer edge when the shaft rotates.

4. The apparatus of claim 1, wherein each blade is canted, each blade having first and second side edges extending between the radial inner and outer edges, wherein the first side edge is axially nearer the outlet and rotationally trailing relative to the second side edge.

5. The apparatus of claim 4, wherein the first side edge of one paddle axially overlaps the second side edge of a next adjacent paddle.

6. The apparatus of claim 1, wherein adjacent shafts are spaced transversely apart from each other and are generally parallel and rotate in opposite directions.

7. The apparatus of claim 1, wherein at least some of the paddles have an arcuate radial outer edge that is shaped to mate with at least one of the inner surfaces.

8. The apparatus of claim 1, wherein each inner surface defines a first sector of a circle having a first radius and a radial outer edge of the each paddle describes a second sector of a circle having a second radius as it rotates, and the second radius is essentially the same as the first radius of at least one of the inner surfaces.

9. The apparatus of claim 1, wherein the conveyance members have fluid injection ports.

10. The apparatus of claim 9, wherein the shaft of a conveyance member comprises a fluid conduit extending longitudinally therethrough.

11. The apparatus of claim 1, wherein the shaft comprises a fluid conduit extending longitudinally therethrough, each paddle further includes a stem, and at least one of the stem and the paddles comprise injection ports.

12. The apparatus of claim 1, wherein the longitudinally extending portions are positioned side-by-side.

13. The apparatus as claimed in claim 1 further comprising a downstream steam explosion hydrolysis reactor.

14. The apparatus as claimed in claim 1 further comprising a heating jacket.

15. The apparatus as claimed in claim 14 wherein the heating jacket is at a temperature from 70 to 90° C.

16. The apparatus as claimed in claim 1 wherein the enclosed volume extends generally horizontally.

17. The apparatus of claim 1, wherein an angle subtended by each of the inner surfaces swept by one of the conveyance members is less than 180 degrees.

18. The apparatus of claim 1, wherein the conveyance members are configured to project the cellulosic feedstock upwardly towards the upper portion.

19. The apparatus of claim 1, wherein the upper outer sides are positioned at a location on an arc described by the longitudinally extending portions that is prior to the arc extending inwardly.

20. The apparatus of claim 1 further comprising a cellulosic feedstock moisture determination stage wherein the amount of moisture required to obtain a predetermined cellulosic feedstock moisture content is determined, and wherein the predetermined amount of moisture is added to the cellulosic feedstock through the fluid injection ports to achieve a cellulosic feedstock moisture content of 30-60 weight % at the outlet of the enclosed volume.

21. An apparatus for conveying a cellulosic feedstock, the apparatus comprising:
(a) a feeder for conveying the cellulosic feedstock into an inlet housing positioned above an inlet of an enclosed volume;
(b) the enclosed volume having a length along which the cellulosic feedstock is conveyed from the inlet located proximate to one end of the enclosed volume to an outlet proximate to an opposed end of the enclosed volume, the enclosed volume having:
  (i) an upper inner arcuate surface having longitudinally extending first and second transversely opposed lower sides;
  (ii) one or more conduits for conveying moisture to a plurality of fluid injection ports located in the upper portion of the enclosed volume for adding moisture to the cellulosic feedstock; and
  (iii) a lower surface comprising a plurality of longitudinally extending portions, each portion having an inner surface that is arcuate in transverse section and has a radius less than the radius of the upper inner arcuate surface;
  wherein one of the longitudinally extending portions has an upper outer side that merges with the first lower longitudinally extending side, and another of the longitudinally extending portions has an upper outer side that merges with the second lower longitudinally extending side; and
(c) a plurality of conveyance members provided within the enclosed volume, each conveyance member being associated with one of the inner surfaces and configured to sweep the one of the inner surfaces and an angle subtended by each of the inner surfaces swept by one of the conveyance members is less than 180 degrees, each conveyance member comprising a longitudinally extending rotary shaft, and a conveying member extending outwardly from the shaft, the conveying member including a plurality of paddles each having a generally planar blade having curved radial outer edge, the paddles being continuously staggered circumferentially along the shaft, wherein the conveying members are spaced from the upper surface whereby the enclosed volume has an upper portion devoid of the conveying members,
wherein the feeder is designed to produce a plug of cellulosic material that inhibits the flow of moisture from the enclosed volume upstream of the feeder.

22. The apparatus of claim 21, wherein the upper outer sides are positioned at a location on an arc described by the longitudinally extending portions that is prior to the arc extending inwardly.

23. The apparatus of claim 21 further comprising a cellulosic feedstock moisture determination stage wherein the amount of moisture required to obtain a predetermined cellulosic feedstock moisture content is determined, and wherein the predetermined amount of moisture is added to the cellulosic feedstock through the fluid injection ports to achieve a cellulosic feedstock moisture content of 30-60 weight % at the outlet of the enclosed volume.

24. An apparatus for conveying a cellulosic feedstock, the apparatus comprising:
(a) a feeder for conveying the cellulosic feedstock into an inlet housing positioned above an inlet of an enclosed volume;
(a) the enclosed volume being generally horizontal and having a length along which the cellulosic feedstock is conveyed from the inlet located proximate to one end of the enclosed volume to an outlet proximate to an opposed end of the enclosed volume, the enclosed volume having a single upper inner curved surface and a lower surface comprising a plurality of longitudinally extending portions, each portion having an inner surface that is arcuate in transverse section and extends generally smoothly and continuously between first and second transversely opposed lower longitudinally extending sides, the first lower longitudinally extending side merged with an upper outer side of one of the longitudinally extending portions and the second lower longitudinally extending side merged with an upper outer side of another of the longitudinally extending portions, the enclosed volume further comprising one or more conduits for conveying moisture to a plurality of fluid injection ports located in the upper portion of the enclosed volume for adding moisture to the cellulosic feedstock; and,
(b) a plurality of conveyance members provided within the enclosed volume, each conveyance member being associated with one of the inner surfaces and configured to sweep the one of the inner surfaces, each conveyance member comprising a longitudinally extending rotary shaft, and a conveying member extending outwardly from the shaft, the conveying member including a plurality of paddles each having a generally planar blade having curved radial outer edge, the paddles being continuously staggered circumferentially along the shaft, wherein the conveying members are spaced from the upper surface whereby the enclosed volume has an upper portion devoid of the conveying members,
wherein the feeder is designed to produce a plug of cellulosic material that inhibits the flow of moisture from the enclosed volume upstream of the feeder.

25. The apparatus of claim 24, wherein the upper outer sides are positioned at a location on an arc described by the longitudinally extending portions that is prior to the arc extending inwardly.

26. The apparatus of claim 24 further comprising a cellulosic feedstock moisture determination stage wherein the amount of moisture required to obtain a predetermined cellulosic feedstock moisture content is determined, and wherein the predetermined amount of moisture is added to the cellulosic feedstock through the fluid injection ports to achieve a cellulosic feedstock moisture content of 30-60 weight % at the outlet of the enclosed volume.

* * * * *